US012558179B2

(12) United States Patent
Hites et al.

(10) Patent No.: US 12,558,179 B2
(45) Date of Patent: Feb. 24, 2026

(54) JOINT STRUCTURES AND RELATED DEVICES AND METHODS

(71) Applicant: INTUITIVE SURGICAL OPERATIONS, INC., Sunnyvale, CA (US)

(72) Inventors: Tibor Hites, Sonora, CA (US); J. Scot Hart, San Carlos, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 888 days.

(21) Appl. No.: 17/771,113

(22) PCT Filed: Oct. 21, 2020

(86) PCT No.: PCT/US2020/056635
    § 371 (c)(1),
    (2) Date: Apr. 22, 2022

(87) PCT Pub. No.: WO2021/081078
    PCT Pub. Date: Apr. 29, 2021

(65) Prior Publication Data

US 2022/0378537 A1     Dec. 1, 2022

Related U.S. Application Data

(60) Provisional application No. 62/925,805, filed on Oct. 25, 2019.

(51) Int. Cl.
    *A61B 34/00*     (2016.01)
    *A61B 17/29*     (2006.01)
    (Continued)

(52) U.S. Cl.
    CPC .............. *A61B 34/71* (2016.02); *A61B 17/29* (2013.01); *B25J 17/0258* (2013.01);
    (Continued)

(58) Field of Classification Search
    CPC ..... A61B 34/71; A61B 17/29; A61B 17/0258; A61B 2034/715; A61B 2017/00327; A61B 2017/00477
    See application file for complete search history.

(56) References Cited

U.S. PATENT DOCUMENTS 4,636,180 A *  1/1987  Runkle ................. B62D 1/187
                                                403/116
6,969,385 B2 * 11/2005  Moreyra ................ A61B 34/71
                                                901/29
(Continued)

FOREIGN PATENT DOCUMENTS

CN        101106945 A    1/2008
JP        5567115 B2    8/2014
            (Continued)

OTHER PUBLICATIONS

International Search Report and Written Opinion for Application No. PCT/US2020/056635, mailed Feb. 9, 2021, 08 pages.

(Continued)

*Primary Examiner* — Monica E Millner
(74) *Attorney, Agent, or Firm* — Jones Robb, PLLC

(57)     ABSTRACT

A joint structure includes a first link and a second link coupled to one another by a joint. The first link and the second link are articulatable relative to each other about the joint. An actuation element extends through a first guide channel in the first link and a second guide channel in the second link. The first guide channel terminates in an opening where the actuation element extends from the first link to extend across the joint to the second link. A first edge portion of the opening is at a first location along a longitudinal axis of the first guide channel, and a second edge portion of the opening is at a second location different from the first (Continued)

location along the longitudinal axis of the first guide channel. Systems and devices include related joint structures.

20 Claims, 17 Drawing Sheets

(51) Int. Cl.
   *B25J 17/02*      (2006.01)
   *A61B 17/00*     (2006.01)
(52) U.S. Cl.
   CPC ............... *A61B 2017/00327* (2013.01); *A61B 2017/00477* (2013.01); *A61B 2034/715* (2016.02)

(56)                References Cited

U.S. PATENT DOCUMENTS

| | | | | |
|---|---|---|---|---|
| 9,220,559 | B2 * | 12/2015 | Worrell | .............. A61B 18/1445 |
| 9,259,275 | B2 * | 2/2016 | Burbank | ................. A61B 34/76 |
| 9,700,334 | B2 * | 7/2017 | Hinman | ................. A61B 17/32 |
| 10,321,927 | B2 | 6/2019 | Hinman | |
| 2011/0022078 | A1 * | 1/2011 | Hinman | ............. A61B 17/2909 |
| | | | | 403/123 |
| 2013/0267936 | A1 | 10/2013 | Stroup et al. | |
| 2016/0183960 | A1 | 6/2016 | Stroup et al. | |
| 2018/0206904 | A1 | 7/2018 | Felder et al. | |
| 2019/0290309 | A1 | 9/2019 | Hinman | |

FOREIGN PATENT DOCUMENTS

| | | |
|---|---|---|
| KR | 101366794 B1 | 2/2014 |
| WO | WO-2012049623 A1 | 4/2012 |
| WO | WO-2019136041 A1 | 7/2019 |

OTHER PUBLICATIONS

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.
Partial European Search Report for Application No. EP20880067.2, mailed on Oct. 17, 2023, 13 pages.
Extended European Search Report for Application No. EP20880067. 2, mailed on Jan. 24, 2024, 12 pages.

* cited by examiner

JOINT STRUCTURES AND RELATED DEVICES AND METHODS

CROSS-REFERENCE TO RELATED APPLICATIONS

This application is a U.S. national stage application under 35 U.S.C. § 371 (c) of International Application No. PCT/US2020/056635, which claims the benefit of priority to U.S. Provisional Application No. 62/925,805 (filed Oct. 25, 2019), titled "JOINT STRUCTURES AND RELATED DEVICES AND METHODS," the entire contents of each of which are incorporated by reference herein.

TECHNICAL FIELD

Aspects of the present disclosure relate to instruments having articulatable joint structures, such as wrists, and related devices, systems, and methods. In particular, aspects of the present disclosure relate to instruments with joint structures that are articulatable in response to forces transmitted by actuation elements extending through links coupled together at joints.

INTRODUCTION

Various tools, such as medical (e.g., surgical) or other industrial instruments often include articulatable joint structures that impart one or more degrees of freedom of movement to such instruments. Such joint structures can include one or more joints, each of which can articulate in one or more degrees of freedom, which may be the same or different.

Articulation of joint structures can be controlled by one or more actuation elements coupled through various components to a manipulator system that receives inputs from a user, such as a surgeon or other operator, to position the instrument as desired. Such manipulator systems can include a teleoperated (e.g., computer-controlled) manipulator system or a manipulator system configured for manual operation. In some cases, it is desirable to that a joint structure exhibit a relatively high stiffness in any given articulation position to facilitate the instrument's ability to maintain a given position under reaction forces, such as those resulting from operation of an end effector of the instrument.

An instrument can include a joint structure coupling the end effector at the distal end portion of the shaft, and articulation of the joint structure can allow the end effector to pivot and be oriented relative to the shaft. The one or more actuation elements extend from the transmission mechanism, through the instrument shaft to link(s) of the joint structure such that forces transmitted by the one or more actuation elements impart articulating movement of the link(s) relative to each other about the joint(s), thereby allowing remote "steering" of the joint structure.

Because the joint structure actuation elements are generally routed in an off-centerline position of the joint structure, articulating (bending) a joint structure results in bending of the actuation element(s). Such repeated bending can lead to changes that affect the path length of the actuation element(s) and can impact other characteristics of the wrist, such as the ability of the articulated joint structure to withstand externally applied loads without deflecting from an intended position.

Additionally, some joint structures include load bearing features that can potentially be compromised by intrusion of environmental materials and debris existing in and/or near the worksite of the instrument. Such intrusion can be prevented by using a protective cover such as a sheath. However, including such a protective cover can result in a relatively greater outside diameter of the instrument compared to an instrument not so equipped. In cases where a minimal overall diameter of the instrument is desired, a sheath may be undesirable.

There exists a need to provide instrument joint structures having improved accuracy and consistency in positioning. There further exists a need to provide instrument joint structures that have sufficient stiffness under applied loads. There also exists a need to provide instrument joint structures that have low susceptibility to intrusion of environmental materials or debris.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one exemplary embodiment, a joint structure includes a first link and a second link coupled to one another by a joint, the first link and the second link being articulatable relative to each other about the joint, and the first link being proximal the second link. An actuation element extends through a first guide channel in the first link and a second guide channel in the second link. The actuation element causes articulating of the first link and the second link relative to each other about the joint in response to tension applied on the actuation element in a proximal direction. The first guide channel terminates in an opening where the actuation element extends from the first link to extend across the joint to the second link, a first edge portion of the opening being at a first location along a longitudinal axis of the first guide channel, and a second edge portion of the opening being at a second location different from the first location along the longitudinal axis of the first guide channel.

In accordance with at least another exemplary embodiment, a medical device includes a first link and a second link disposed in series in a proximal-to-distal direction and defining an articulatable member. An actuation element extends in the proximal-to-distal direction through a first guide channel of the first link and through a second guide channel of the second link. In an unarticulated state of the articulatable member, a portion of the actuation element between the first guide channel of the first link and the second guide channel of the second link is positioned a first radial distance from a longitudinal centerline of the articulatable member. In an articulated state of the articulatable member and on a convex side of an articulated shape of the articulatable member, the portion of the actuation element between the first guide channel of the first link and the second guide channel of the second link is positioned a second radial distance from the longitudinal centerline of the articulatable member. The second radial distance is greater than the first radial distance.

In accordance with yet another exemplary embodiment, a joint structure includes a first link and a second link coupled to one another by a joint. The first link and the second link are articulatable relative to each other about the joint, and the first link is proximal the second link. An actuation element extends through a first guide channel in the first link and a second guide channel in the second link. The actuation element causes articulating of the first link and the second link relative to each other about the joint in response to tension applied on the actuation element in a proximal direction. On the condition the joint structure is in an articulated state, the actuation element lies at a first radial distance from a centerline of the joint on the condition the actuation element is on a concave side of the articulated joint structure. The actuation element lies at a second radial distance from the centerline of the joint on the condition the actuation element is on a convex side of the articulated joint structure, the second radial distance being different from the first radial distance.

In accordance with yet another exemplary embodiment, a joint structure includes a first link and a second link coupled to one another by a joint, and the first link and the second link are articulatable relative to each other about the joint. The first link is proximal to the second link. An actuation element extends through a first guide channel in the first link and a second guide channel in the second link, and the actuation element causes articulating of the first link and the second link relative to each other about the joint in response to tension applied on the actuation element in a proximal direction. The first guide channel terminates in an opening where the actuation element extends from the first link to extend across the joint to the second link, and the opening lies in a plane having a non-perpendicular angle to a longitudinal axis of the first guide channel.

In accordance with yet another exemplary embodiment, a medical instrument includes a shaft, an end effector, and a wrist coupling the end effector to a distal end portion of the shaft. The wrist includes a first link and a second link coupled to one another by a joint. The first link and the second link are articulatable relative to each other about the joint, and the first link is proximal the second link. An actuation element extends through a first guide channel in the first link and a second guide channel in the second link. The actuation element causes articulating of the first link and the second link relative to each other about the joint in response to tension applied on the actuation element in a proximal direction. The first guide channel terminates in an opening where the actuation element extends from the first link to extend across the joint to the second link. A first edge portion of the opening is at a first location along a longitudinal axis of the first guide channel, and a second edge portion of the opening is at a second location different from the first location along the longitudinal axis of the first guide channel.

In accordance with yet another exemplary embodiment, a medical instrument includes a shaft, an end effector, and a wrist coupling the end effector to a distal end portion of the shaft. The wrist includes a first link and a second link coupled to one another by a joint. The first link and the second link are articulatable relative to each other about the joint, and the first link is proximal the second link. An actuation element extends through a first guide channel in the first link and a second guide channel in the second link. The actuation element causes articulating of the first link and the second link relative to each other about the joint in response to tension applied on the actuation element in a proximal direction. The first guide channel terminates in an opening where the actuation element extends from the first link to extend across the joint to the second link, the opening lying in a plane having a non-perpendicular angle to a longitudinal axis of the first guide channel.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and they are incorporated in and constitute a part of this specification. The drawings illustrate one or more exemplary embodiments of the present disclosure and, together with the description, explain certain principles and operation. In the drawings.

Figure 1:
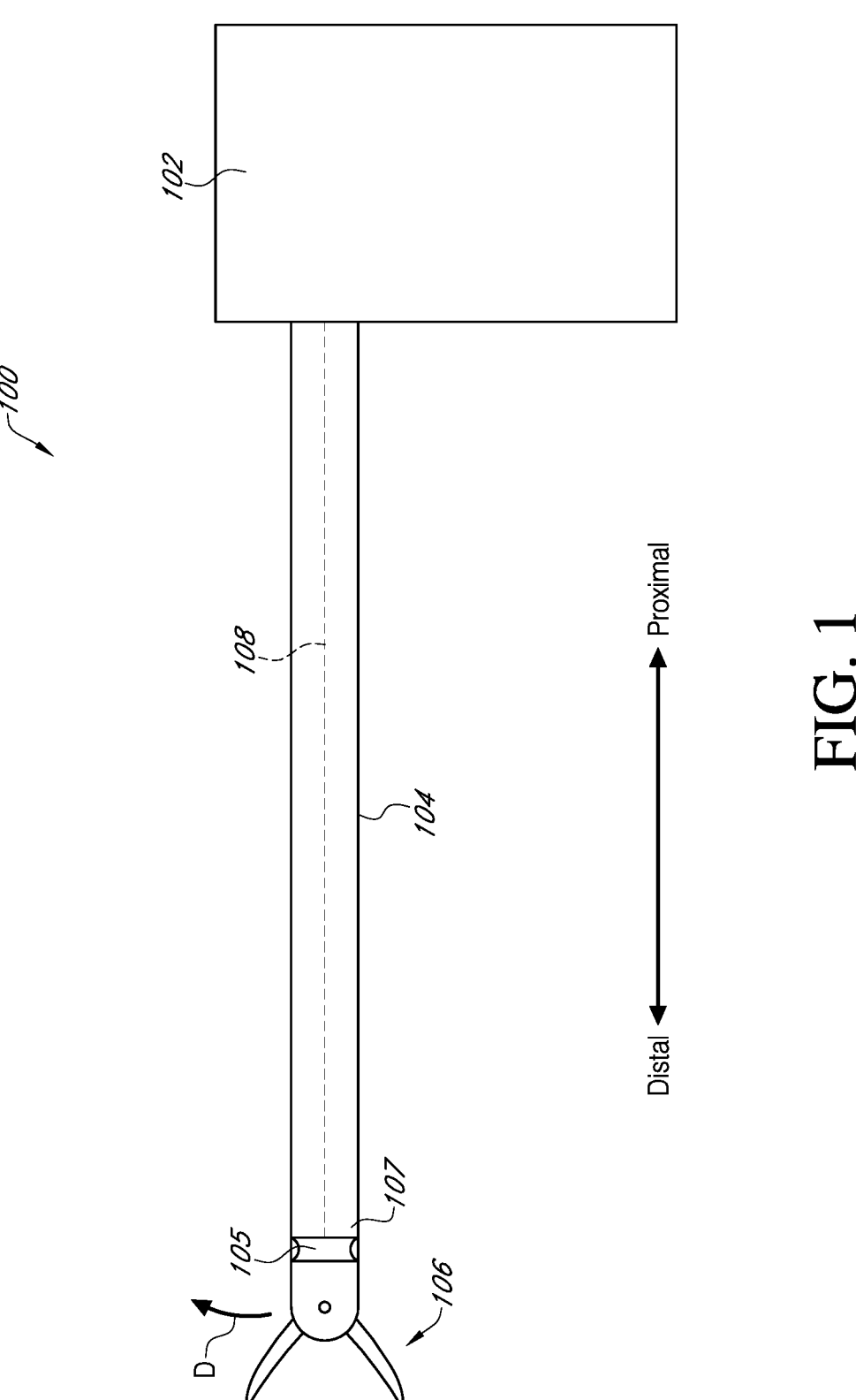
FIG. 1 is a schematic view of an instrument comprising a joint structure in the form of a wrist according to the present disclosure.

5
6

DETAILED DESCRIPTION

The present disclosure contemplates joint structures, such as, but not limited to wrists, that include features that can provide desired stiffness and predictable movement, e.g., during articulation. Various embodiments of the present disclosure contemplate the modification of a path along which one or more actuation elements extend across a joint structure. For example, various embodiments of the present disclosure use an asymmetrical configuration of the paths of actuation elements that are positioned diametrically across from each other along the instrument joint structure. This configuration can permit controlled and a relatively large range of articulation a joint structure, while also maintaining relatively high stiffness to permit accurate positioning of the joint structure during bending as well as returning to a neutral (straight) configuration after bending. Moreover, such a configuration can provide sufficient stiffness to the joint structure in the bent position to avoid buckling under a compressive force acting along a longitudinal axis of the joint structure.

In various disclosed embodiments, asymmetrical actuation element paths across a joint is achieved through the configuration of guide channels in the links of the joint that receive and route the actuation elements across the joint between adjacent links. For example, the channels can have channel support portions terminating at different locations relative to the longitudinal axis centerline defined by the links of the joint. For example, the location of termination of an actuation element channel support portion can depend on the radial distance from the longitudinal axis. A first support portion of the actuation element guide channel can terminate at an edge portion at a first longitudinal location, and a second support portion of the channel can terminate at a second edge portion at a longitudinal location different from the first longitudinal location. In other words, terminal locations of the support portions of the actuation element guide channel are asymmetrical relative to a centerline of the channel. The first portion can be an inner circumferential portion of the channel and the second portion can be an outer circumferential portion of the channel, with the inner and outer being relative to a radial distance from a longitudinal centerline of the joint. Such an arrangement can provide support to the actuation element at different regions of the actuation element depending on whether the actuation element lies along an outer portion or an inner portion of a bend in a bent position of the joint. For example, the outer portion corresponds to a longer path of the actuation element across a joint along the convex portion of the bend, and the inner portion corresponds to a shorter path of the actuation element across the joint along the concave portion of the bend.

Such arrangements of asymmetrical termination locations of the actuation element guide channel can alter the geometric relationships between the actuation elements and the links of the joint structure. The differing support regions of the actuation element guide channel define the distance from the actuation element to a longitudinal centerline of the joint structure, i.e., the moment arms with which the actuation elements acts on the links of the joint structure when the joint structure is articulated. The configuration of the support regions of the actuation element guide channel can be chosen to tailor the moment arms to provide the tensioned actuation element with sufficient leverage on the links of the joint structure to provide a desired level of stiffness.

The longitudinal locations at which the actuation element guide channel support regions terminate can differ and be chosen based on various desired outcomes. To provide differing longitudinal locations at which an actuation element guide channel terminates, the opening of the guide channel can be provided in an oblique plane relative to the longitudinal centerline of the guide channel. In embodiments of joint structures that include links with complementary contact surfaces, such as rolling contact surfaces, the actuation element guide channels can have support regions that are non-planar with roll axes of the rolling contact surfaces. In some exemplary embodiments, the oblique opening and thus the longitudinal locations of the support regions of the actuation element as it leaves the channel and crosses the joint can be chosen to provide a greater moment arm with which the actuation element acts on links of the joint structure. In some exemplary embodiments, the longitudinal locations can be chosen such that the free path length of the actuation elements are tailored to compensate for slack that would otherwise develop in one or both of the actuation elements as the joint structure is articulated. Such an arrangement can also contribute to stiffness of the joint structure by eliminating undesirable slack in one or both actuation elements.

The present disclosure further contemplates joint structures that include features to minimize or prevent environmental materials (e.g., tissue or other material located at a surgical site) from interfering with mechanical components. For example, in some exemplary embodiments, the actuation element guide channel exits of the present disclosure position the actuation elements such that they are outboard of other interfacing components of the joint structure, such as, for example, contacting bearing surfaces and/or intermeshing teeth or other gear components of adjacent links of the joint structure. Outboard positioning of the actuation elements can contribute to minimizing or preventing environmental materials from interfering with the mechanical components.

In some exemplary embodiments, the joint structures of the present disclosure include rolling contact surfaces having relieved portions proximate an outer surface of links of the joint structure. The relieved portions provide a gap between portions of the rolling contact surfaces, which can be sized so as to prevent material at a worksite surrounding the instrument (e.g., tissue at a surgical site) from being pinched between the rolling contact surfaces. Such features can be used in combination with actuation element guide channels having differing support regions resulting in asymmetrical termination locations as described above. Optionally, such relieved portions can be used in combination with joint structures that include other actuation element and guide channel arrangements.

Referring now to FIG. 1, a schematic side view of an embodiment of an instrument 100 (such as, for example, a surgical instrument) is shown. While aspects of the present disclosure are discussed in the context of surgical instruments with joint structures in the form of wrists supporting an end effector of the instrument, embodiments of the present disclosure can be used with various instruments used in medical procedures. For example, such instruments include those used for diagnosis, therapy, and sensing, including, for example, imaging instruments such as endoscopes and other imaging instruments. Accordingly, medical instruments as used herein encompasses a variety of instruments used in surgical, diagnostic, and therapeutic applications. In addition, aspects of the disclosure can have non-surgical applications, such as in other remotely-actuatable instruments for inspection and other industrial uses, general robotic uses, manipulation of non-tissue work pieces, etc.

The instrument 100 includes a shaft 104 with a transmission mechanism 102 at a proximal end portion of the shaft 104 and an end effector 106 at a distal end portion 107 of the shaft. In an exemplary embodiment, the transmission mechanism 102 is configured to interface with a manipulating system, such as manipulating systems shown below in connection with FIGS. 15 and 16, respectively. Alternatively, the transmission mechanism 102 can be configured to be operated manually such as for a manual, laparoscopic instrument, which may have a handle or other arrangement configured to be manipulated directly by a user.

The end effector 106 is coupled at the distal end portion 107 of the shaft 104 by a joint structure 105, which may include one or more articulatable joints to impart one or more degrees of freedom of movement to the end effector 106 relative to the shaft 104 (for example, to move the end effector 106 in one or more of pitch and yaw). Thus, a joint structure 105 can include two links coupled together by a joint, or a series of more than two links coupled by a series of joints. For ease and simplification, the embodiments discussed below show two links and a single joint referred to below as a joint structure, but the principles disclosed herein can be applied to joint structures that have more than two links and more than one joint, as those having ordinary skill in the art would be familiar with. Moreover, joint structures in accordance with exemplary embodiments can include a series of links connected with joints wherein one or more of the joints have the same or different axes about which they articulate the joined links.

Certain coordinated movements of multiple joints can enable, for example, pivoting of the end effector 106, longitudinal translations, combined movement in pitch and yaw directions, or other compound movements of the end effector 106 in multiple degrees of freedom relative to the instrument shaft 104. While a single actuation element 108 is shown in connection with FIG. 1, other, additional actuation elements may also be operably coupled between the transmission mechanism 102 and the joint structure 105 to actuate articulation D of the joint structure 105 along various degrees of freedom associated with individual joints (such as individual wrists) of the joint structure 105.

Figure 15:
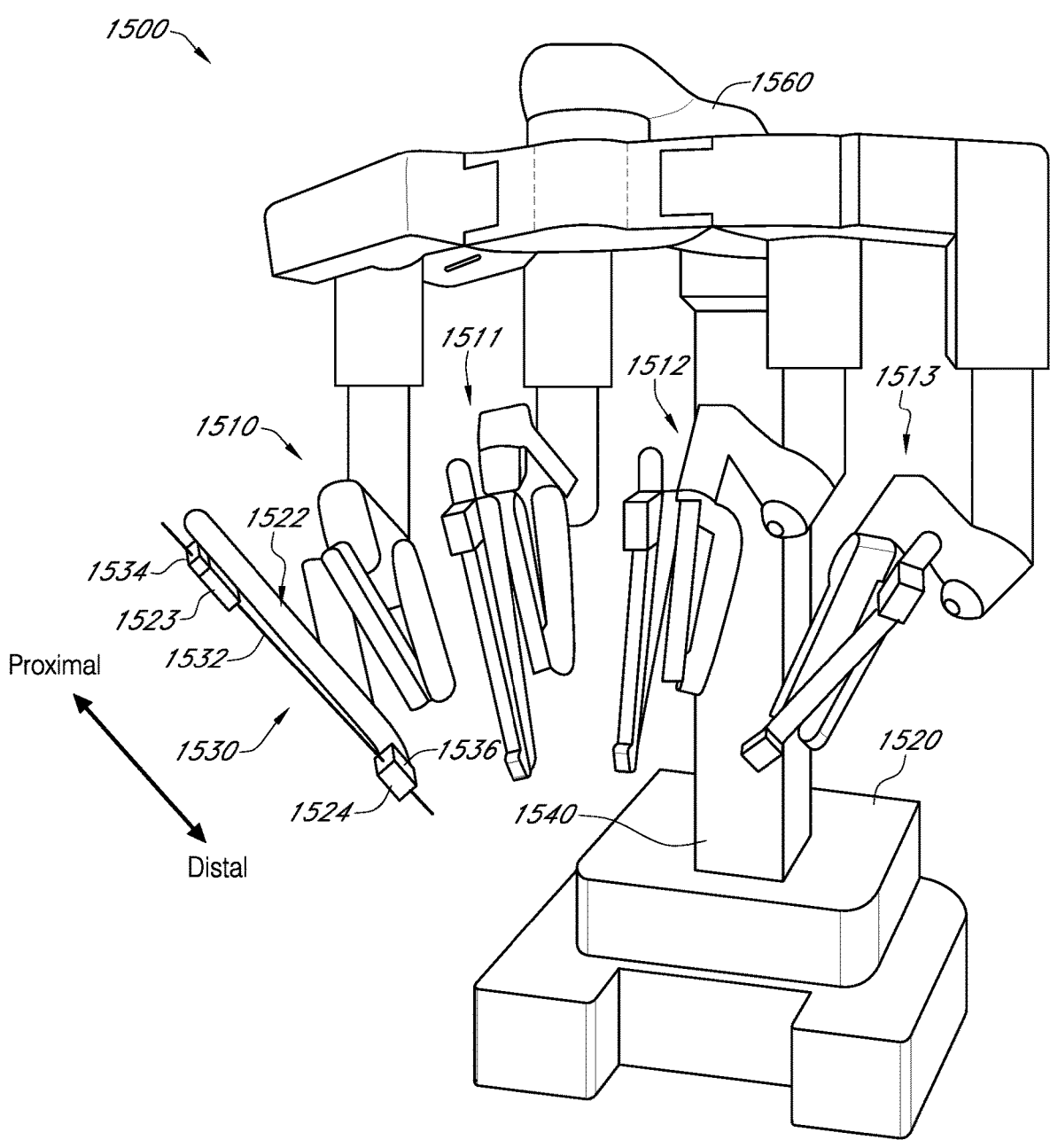
FIG. 15 is a perspective view of a manipulating system according to an exemplary embodiment of the disclosure.
Figure 16:
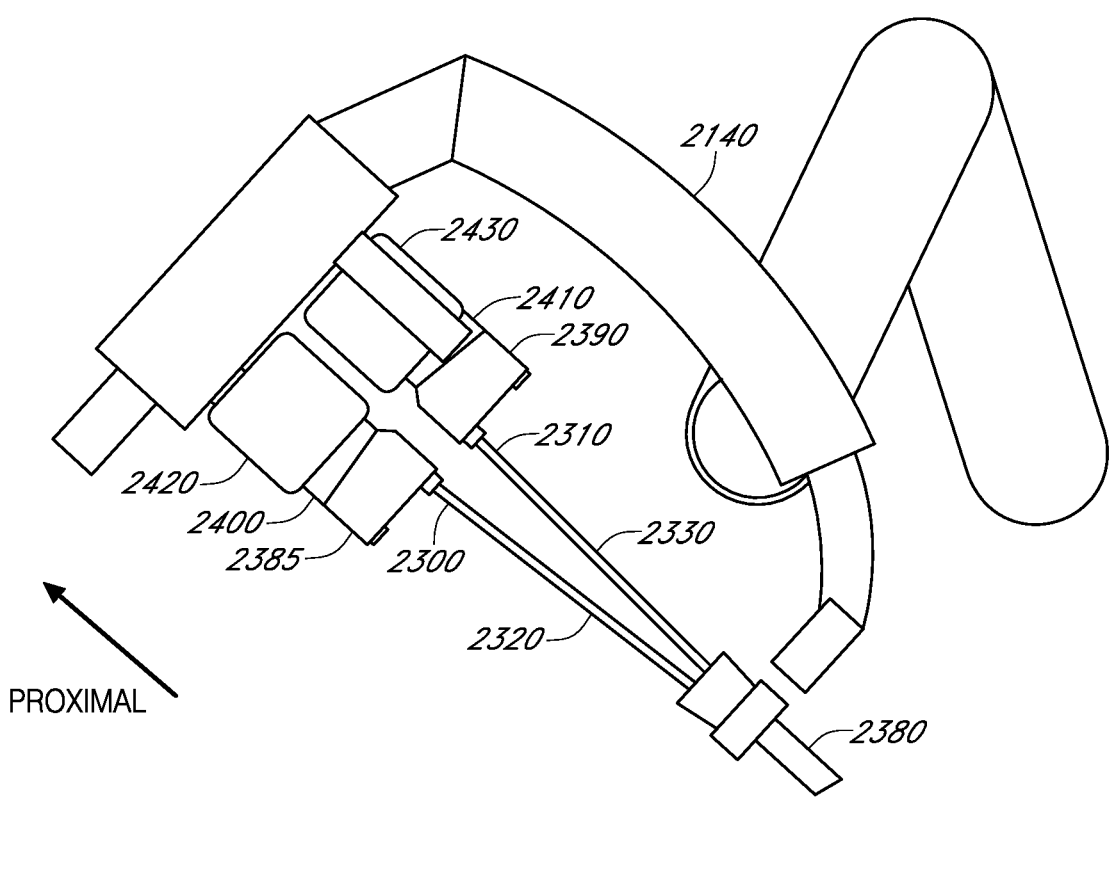
FIG. 16 is a partial schematic view of an embodiment of a manipulator arm of a manipulating system according to the present disclosure with two instruments in an installed position.

Operation of the end effector 106 can be controlled by manipulation of the transmission mechanism 102, either manually or through drives of a manipulating system (e.g., the manipulating systems shown in FIGS. 15 and 16). The transmission mechanism 102 includes various mechanical and/or electromechanical devices that transmit motion, energy, and/or signals, e.g., from the manipulating system, or from inputs at the transmission mechanism 102 operable by a user, to the end effector 106. For example, one or more actuation elements (one actuation element 108 shown in FIG. 1) can extend from the transmission mechanism 102, through the shaft 104, and to the end effector 106, to operably couple the transmission mechanism 102 (or a component therein) to the end effector 106. Force applied to the actuation element 108 by the transmission mechanism 102 can actuate (e.g., close, open, or otherwise control) the end effector 106. While the end effector 106 shown in FIG. 1 comprises a pair of opposing jaw members, other end effector configurations, such as staplers, clip appliers, ligation tools, and other tools are considered within the scope of this disclosure. In various embodiments, actuation elements may comprise flexible members, such as polymer or metal (e.g., tungsten) solid or braided actuation elements.

Figure 2:
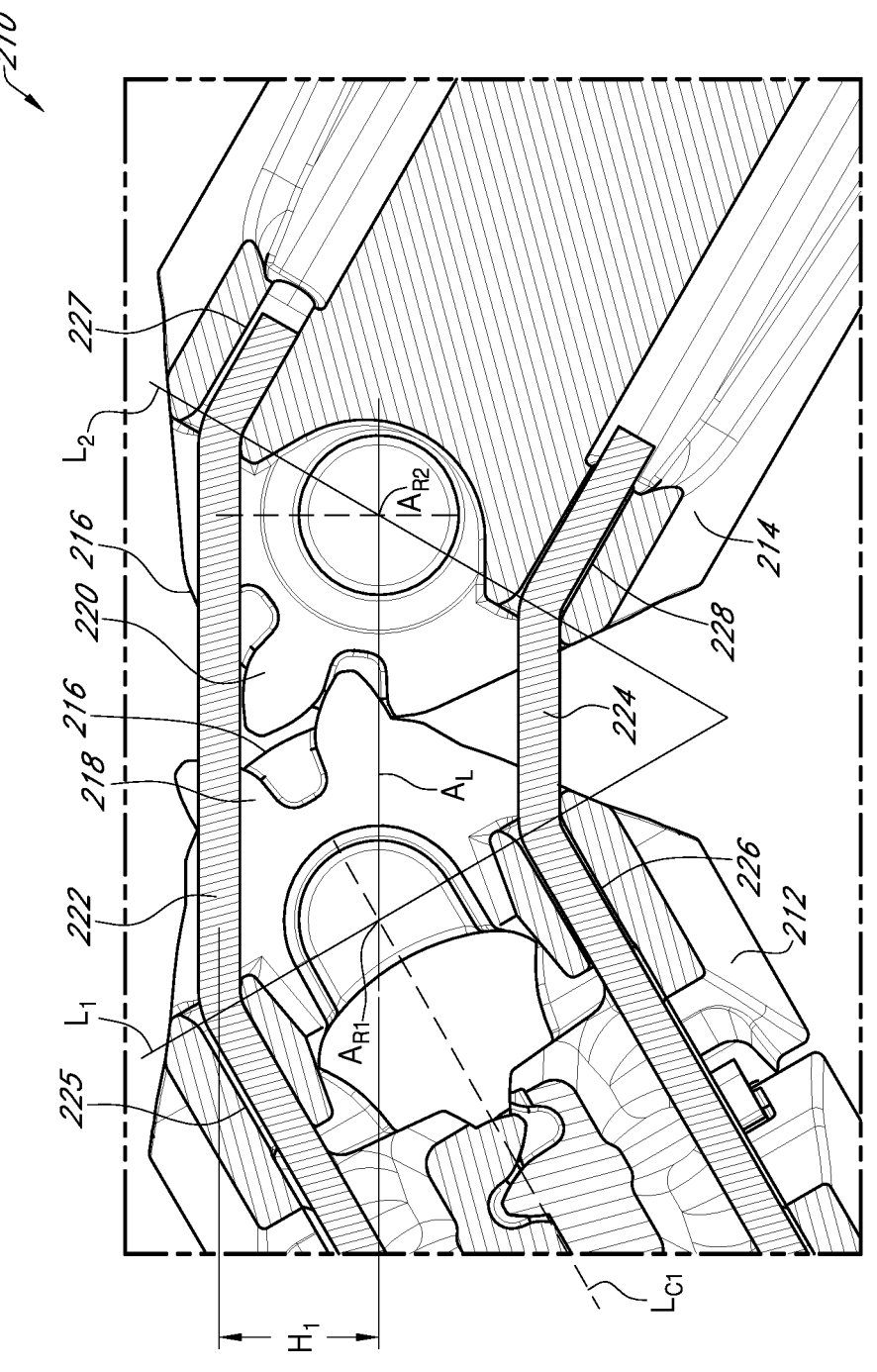
FIG. 2 is a longitudinal cross-sectional, schematic view of an instrument joint structure having symmetrical actuation element path lengths across the joint structure.

Referring now to FIG. 2, a side view of a joint structure 210 according to the prior art is shown. The joint structure 210 joins a first link 212 and a second link 214 at opposed, radiused contact surfaces 216 that define rolling axes $A_{R1}$, $A_{R2}$ about which each of a first link 212 and second link 214 respectively rotate as the joint structure 210 is articulated. The joint structure 210 includes intermeshing components 218 and 220 that prevent slippage between the first link 212 and second link 214 as the joint structure 210 is articulated. While exemplary embodiments of the present disclosure are shown and described herein with reference to joint structures having radiused contact surfaces such as 216, aspects of the disclosure are equally applicable to joint structures and other joint structures having other kinematic control components such as pinned joints and other configurations of articulable and/or flexible joints. Further, while the description and drawings herein show joint structures having a single degree of freedom, aspects of the present disclosure are also applicable to joint structures having multiple joints and thus multiple degrees of freedom, such as parallel motion mechanisms or other series of joints.

One or more actuation elements extend through the joint structure 210. As discussed above in connection with FIG. 1, the one or more actuation elements may be operatively coupled to the transmission mechanism 102 (FIG. 1) to actuate articulation of the joint structure 210. In the exemplary embodiment of FIG. 2, two actuation elements 222 and 224 are visible. To actuate articulation of the joint structure 210 from a neutral position (not shown) to the position shown in FIG. 2, the actuation element 222 is tensioned while the actuation element 224 is slackened. Simultaneous tensioning and slackening can be effectuated by coupling the actuation elements 222 and 224 to a single capstan in the transmission mechanism 102 (FIG. 1) such that as the capstan is rotated, one actuation element pays out while the other actuation element simultaneously pays in. In some configurations, the actuation elements 222 and 224 may represent two portions of a single actuation element with a midportion that is wrapped around a capstan. Thus, as used herein, the actuation elements 222 and 224 can represent individual actuation elements, or separate portions of a single actuation element. The arrangement of actuation elements 222 and 224 in FIG. 2 can be referred to as a "pull-pull arrangement." Simultaneous tensioning and relaxing of the opposing actuation elements create a couple that rotates (i.e., articulates) the joint about an axis of articulation. While the exemplary embodiments discussed herein feature a "pull-pull" arrangement, other arrangements of actuation elements, such as push-pull or other configurations, are encompassed by the present disclosure.

As shown in FIG. 2, the actuation elements 222 and 224 extend through respective actuation element guide channels 225, 226 in the first link 212 and through actuation element guide channels 227, 228 in the second link 214. In the joint structure configuration of FIG. 2, the actuation element guide channels 225, 226 in the first link 212 terminate in a plane $L_1$ that is coplanar with the roll axis $A_{R1}$ and is normal to the longitudinal axes of the actuation element guide channels 225, 226 of the first link 212. Similarly, the actuation element guide channels 227, 228 of the second link 214 terminate in a plane $L_2$ that passes through the roll axis $A_{R2}$ and is normal to the longitudinal axes of the actuation element guide channels 227 and 228. Geometrically, this configuration promotes conservation of the path lengths of the actuation elements 222 and 224 (i.e., the sum of the path lengths of the actuation element guide channels remains unchanged) as the joint structure 210 is articulated from a neutral position. Stated another way, as the joint structure 210 is articulated from the neutral position, a reduction in distance between the actuation element guide channels 226 and 228 on the inside of the joint structure 210 is offset by an equal increase in distance between the actuation element guide channels 225 and 227 on the outside of the joint structure 210. This configuration can be desirable for joint architectures in which the actuation elements 222 and 224 represent separate cables or different portions of a single cable or other member wrapped around a capstan in the transmission mechanism (e.g., transmission mechanism 102 in FIG. 2). For example, as a portion of the actuation element 222 pays out from the capstan, an equal portion of actuation element 224 is wound onto the capstan, thus preventing significant slack development on either side of the joint structure 210.

When the joint structure 210 is in a neutral position, a moment arm with which the actuation elements 222 and 224 act on the segments to articulate the joint structure 210 is equal to a distance from the plane $A_L$ in which the axes $A_{R1}$ and $A_{R2}$ lie to the centerline of the respective actuation element guide channels 226, 228. In FIG. 2, the joint structure 210 is shown articulated from the neutral position. As the joint structure 210 articulates from the neutral position, the moment arms with which the actuation elements 222 and 224 act on the segments to articulate the joint structure 210 effectively change based on the degree of articulation of the joint structure 210. For example, when the joint structure 210 is articulated to an angle of 45 degrees between the first segment 212 and second segment 214, the moment arm effectively reduces in length because the unsupported length of actuation elements 222 and 224 between the actuation element guide channels 225, 226, 227, 228 draw closer to the plane $A_L$ passing through the axes $A_{R1}$ and $A_{R2}$. That is, considering the actuation element 222 and the first segment 212, the moment arm becomes equal to the distance $H_1$, which is the distance from the line $A_L$ to the actuation element 222, when the segments are articulated relative to one another. The distance $H_1$ can be calculated by multiplying the cosine of the angle between the plane $A_L$ passing through the axes $A_{R1}$ and $A_{R2}$ and a longitudinal centerline $L_{C1}$ of the first segment 212. As is apparent from FIG. 2, the distance $H_1$ is less than the length from the axis $A_{R1}$ to the centerline of the guide channel 225 lying in the plane $L_1$, and thus the actuation element 222 acts on the first link 212 with a shorter moment arm when the first link 212 and second link 214 are articulated with respect to one another. The moment arms with which each of actuation elements 222, 224 acts on first link 212 and second link 214 are similarly reduced.

Because the position of the first and second links 212, 214 relative to one another is controlled and maintained at least in part by the actuation elements 222, 224, a reduction in the moment arm with which the actuation elements 222, 224 act on the first and second links 212, 214 correspondingly increases the force applied to the actuation elements 222, 224 when the first and second links 212, 214 are subjected to external forces, such as reaction forces applied to the instrument (e.g., instrument 100 in FIG. 1) during use. As a result, the "stiffness" of the joint structure 210 (i.e., the ability of the joint structure 210 to withstand applied external forces without deflecting from an intended position under the applied external force) is reduced as the angle of articulation of the joint structure 210 is increased.

The present disclosure contemplates actuation element guide channels having configurations that modify the effective moment arm as the angle between joint structure links changes. Actuation element guide channels having such a configuration can provide conservation of length of the actuation elements, or, in some embodiments, provide near-conservation of length that is sufficiently close to true conservation of length as to avoid any excessive slack or excessive tension as the joint structure articulates through its angular travel.

Figure 3:
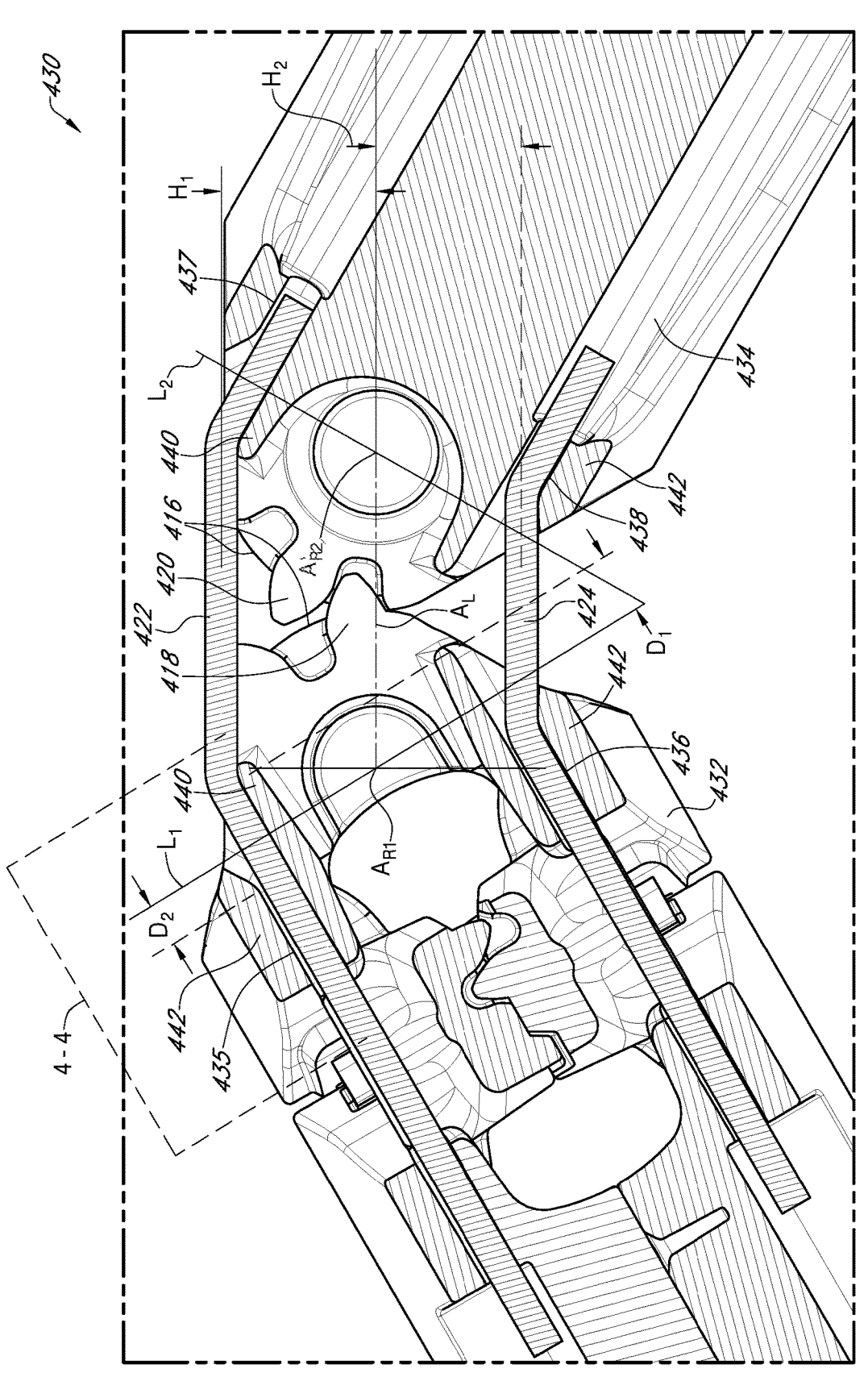
FIG. 3 is a longitudinal cross-sectional, schematic view of an instrument joint structure having asymmetrical actuation element path lengths across a joint structure according to an embodiment of the present disclosure.

Referring now to FIG. 3, a joint structure 430 according to the present disclosure is shown and has a structure generally similar to that described with reference to FIG. 2. The joint structure 430 includes a first link 432 and a second link 434 that articulate relative to one another by a joint comprising rolling contact surfaces 416, which define axes of articulation $A_{R1}$ and $A_{R2}$. As with the joint structure 210 shown and described in connection with FIG. 2, the joint structure 430 includes intermeshing components 418 and 420 that prevent slippage between the first link 432 and second link 434 as the joint structure 430 is articulated. Such intermeshing components are optional, and some exemplary embodiments of the present disclosure do not include such intermeshing components.

Each of the first link 432 and second link 434 include actuation element guide channels 435, 436 and 437, 438, respectively. Actuation elements 422 and 424 each pass through respective actuation element guide channels 435, 436 and 437, 438, and coordinated tensioning and letting out of the actuation elements 422 and 424 (e.g., controlled by the transmission mechanism 102 in FIG. 1). The actuation element guide channels 435, 436 and 437, 438 include features that change the effective moment arm with which the actuation elements 422 and 424 act on the first and second links 432 and 434 depending on the angle of articulation between the first and second links 432 and 434.

For example, as shown in FIG. 3, each actuation element guide channel 435, 436 and 437, 438 terminates at an edge portion that is offset with respect to planes $L_1$ and $L_2$. Stated another way, the edge portions of actuation element guide channels 435, 436 and 437, 438 do not lie in the planes $L_1$ and $L_2$, but rather the edge portions are configured such that the actuation elements 422 and 424 exit the channels 435, 436 and 437, 438 at different longitudinal positions of the actuation elements 422 and 424 depending on the distance from the plane $A_L$ in which the axes of articulation $A_{R1}$ and $A_{R2}$ lie. In other words, a line passing through the support portions where a channel (e.g., channel 435) terminates forms an oblique angle with respect to a longitudinal axis of the channel. In this way, the configuration of the actuation element guide channels 435, 436 and 437, 438 can be used to alter the moment arm with which the actuation elements 422 and 424 act on the first link 432 and second link 434 depending on the angle of articulation of the joint structure 430, as discussed further below. For brevity of description, actuation element guide channels 435 and 437 are discussed in particular below, but all of actuation element guide channels 435, 436 and 437, 438 can include corresponding features.

As shown in FIG. 3, the actuation element guide channel 435 has an inner portion 440 that extends a distance $D_1$ parallel to the length of the actuation element guide channel 435 beyond (i.e., in a direction towards the second link 434) the plane $L_1$. The actuation element guide channel 435 has an outer portion 442 that terminates a distance $D_2$ before (i.e., in a direction away from the second link 434) the plane $L_1$. In the exemplary embodiment of FIG. 3, Each of the four actuation element guide channels 435, 436, 437, 438 has a similar configuration with inner portions 440 and outer portions 442.

In FIG. 3, the joint structure 430 is shown articulated at approximately a 60-degree angle between the first link 432 and second link 434. For the purposes of this description, the "inside" of the articulated joint structure 430 is the portion of the joint structure 430 on the interior of the bend angle (i.e., below the centerline of the various components in the view of FIG. 3) and the "outside" of the articulated joint structure 430 is the portion of the joint structure 430 on the exterior of the bend angle (i.e. above the centerline of the various components in the view of FIG. 3). Stated another way, "outer" or "outside" refers to the convex portion of the bend of the joint and "inner" or "inside" refers to the concave portion of the bend of the joint.

As shown in FIG. 3, the outer actuation element 422 contacts the inner portion 440 of the actuation element guide channels 435 and 437 as the joint structure 430 articulates. Because the inner portions 440 of the actuation element guide channels 435 and 437 do not terminate in the planes $L_1$ and $L_2$, the actuation element 422 is positioned further outward from a line passing through the axes of rotation $A_{R1}$ and $A_{R2}$ as compared to the design discussed in connection with FIG. 2. That is, in the embodiment of FIG. 3, as the joint structure 430 is articulated from a neutral position, the moment arm with which the actuation element 422 acts on the links 432 and 434 initially increases and reaches a maximum $H_1$ when a line passing through the axis $A_{R1}$ and the actuation element support portion 440 is perpendicular to the plane $A_L$ in which the axes of rotation $A_{R1}$ and $A_{R2}$ lie.

As shown in FIG. 3, the actuation element 424 on the inside of the joint structure 430 breaks over the outer portions 442 of the actuation element guide channels 436 and 438 as the joint structure 430 articulates. Because the outer portions 442 do not terminate in planes $L_1$ and $L_2$, but rather terminate a distance $D_2$ before the plane $L_1$ (i.e., on a side of the plane $L_1$ opposite the contact surfaces 416) the actuation element 424 is positioned further outward from the line passing through $A_{R1}$ and $A_{R2}$ as compared to the embodiment discussed in connection with FIG. 2. That is, the moment arm $H_2$ with which the actuation element 424 acts on the links 432 and 434 as the joint structure 430 articulates is greater than the corresponding moment arm in the embodiment of FIG. 3.

The distances of $D_1$ and $D_2$, and thus the effective moment arms with which the actuation elements act on the joint structure links as the joint structure is articulated, can be chosen based on desired characteristics of the joint structure 430. For example, in the embodiment of FIG. 3, the distances $D_1$ and $D_2$ are equal, which configuration provides conservation of length of the combined paths of the actuation elements 422 and 424 throughout the range of motion of the joint structure 430. With this configuration, the moment arms $H_1$ and $H_2$ are also equal as they vary throughout the range of articulation of the joint structure 430. In some embodiments, the distances $D_1$ and $D_2$ are chosen to be unequal. While such arrangements may impact length conservation of the actuation elements, $D_1$ and $D_2$ can be chosen to "tune" the joint structure 430 with the desired characteristics, as discussed below in connection with the example embodiments of FIGS. 6-10.

One example of an arrangement where differing distances $D_1$ and $D_2$ may be desired is a configuration in which the joint structure 430 has relatively high intrinsic stiffness, e.g., due to presence of an outer sheath, an internal drive member, or other component extending along the joint structure and exhibiting flexural elasticity. In such a configuration, the resilience of the sheath, drive member, or other componentry can cause the tension in the inner actuation element (i.e., the control actuation element on the "inside" of the joint structure as it articulates) to be greater than the outside actuation element, resulting in the inner actuation element stretching and the outer actuation element developing slack. Slack development results in a loss of stiffness of the joint structure as external reaction forces or internal forces (such as tension or compression in the drive member) act on the joint structure.

According to embodiments of the present disclosure, joint structures can be configured with unequal distances $D_1$ and $D_2$ to compensate for such slack development. For example, in configurations in which $D_1$ is greater than $D_2$, the actuation element path length is not conserved but becomes longer as the angle of joint structure articulation is increased. In this manner, the slack that otherwise would develop in the outside actuation element is compensated for by the increased path length as the joint structure articulates, thereby contributing to increased joint structure stiffness compared to conventional joint structure designs.

Figure 4:
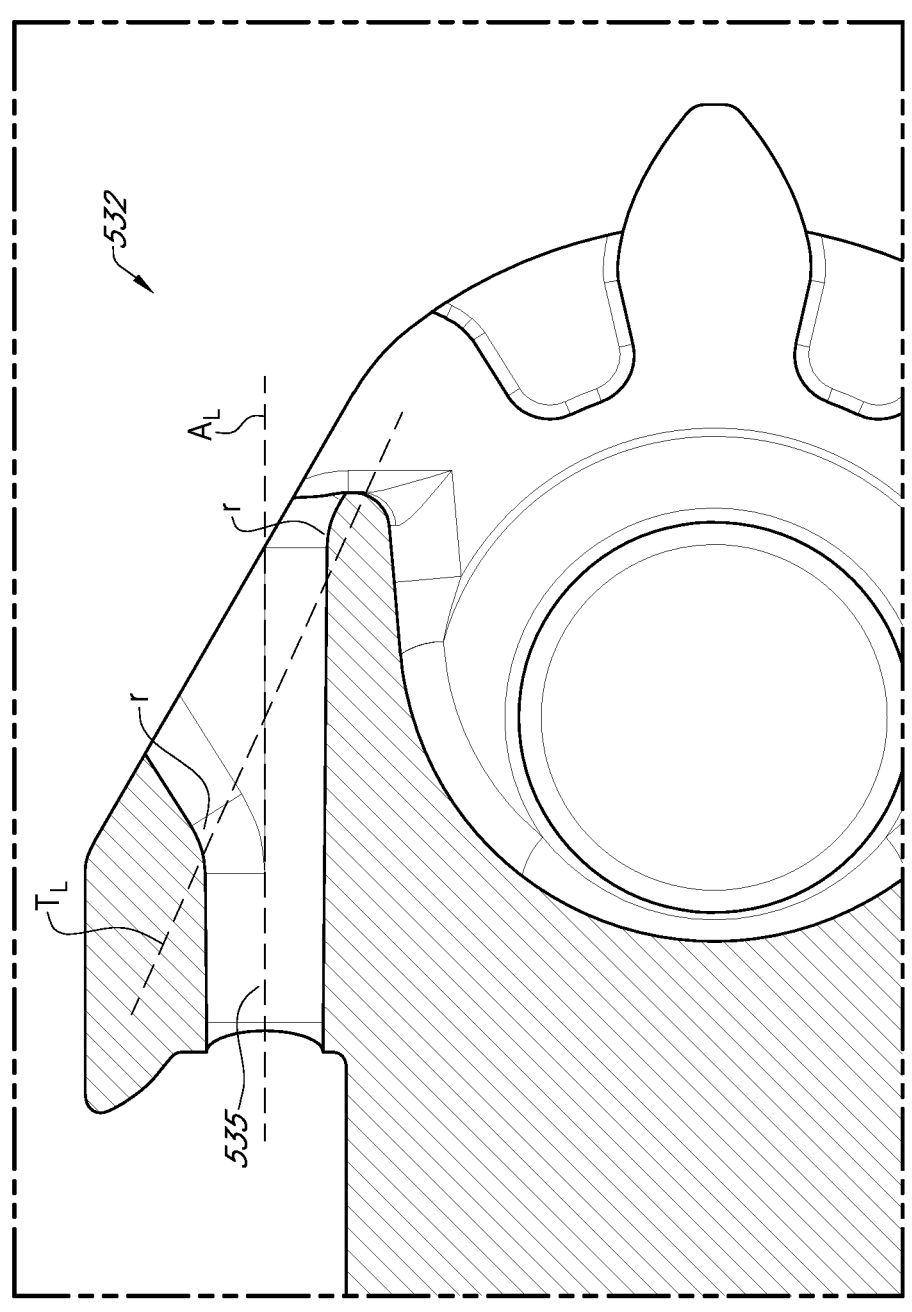
FIG. 4 is a detailed view of portion 4-4 of FIG. 3 showing an exemplary configuration of an actuation element guide channel through a link of the joint structure of FIG. 3.

Referring now to FIG. 4, an enlarged view of a link 532 of a joint structure according to an embodiment of the present disclosure is shown to more clearly illustrate various aspects of the disclosure. An actuation element guide channel 535 extends along a longitudinal axis $A_L$ of the link 532. The actuation element guide channel 535 terminates along a line $T_L$ that is at an oblique angle to the longitudinal axis $A_L$. In the embodiment of FIG. 5, the cross-sectional shape of the actuation element guide channel 535 is a circle. Thus, along the line $T_L$, the guide channel 535 has a generally elliptical opening. Other exemplary embodiments can feature non-circular guide channel cross-sectional shapes, such as, without limitation, rectilinear shapes, polygonal shapes, ovoid shapes, etc. In the exemplary embodiment of FIG. 4, a portion of the actuation element guide channel 535 over which actuation elements (e.g., actuation elements 422 and 424 shown in FIG. 3) bend as the joint structure is articulated are radiused with a radius r. The radius r is optional and can contribute to reducing (e.g., minimizing) friction of the actuation elements against the actuation element guides as the joint structure is articulated, and can also lessen stress in the actuation element by increasing the bend radius of the actuation element. In exemplary embodiments of the disclosure, the radius r can be, for example, in a range from 0 to 0.1 inches (2.54 mm). In the embodiment of FIG. 4, the radius r is 0.033 inches (0.838 mm). Other values of r, such as other values between 0 and 0.1 inches, or values of above 0.1 inches, are within the scope of the present disclosure. Such variations in radius r can also influence the actuation element path lengths as the wrist is articulated. For example, an increase in the radius r on one side of a guide channel, all other parameters being equal, can have a similar effect on path length and moment arm as altering the distance $D_1$ or $D_2$. In other exemplary embodiments, the actuation element guide channels do not include a radius r.

Figure 5A:
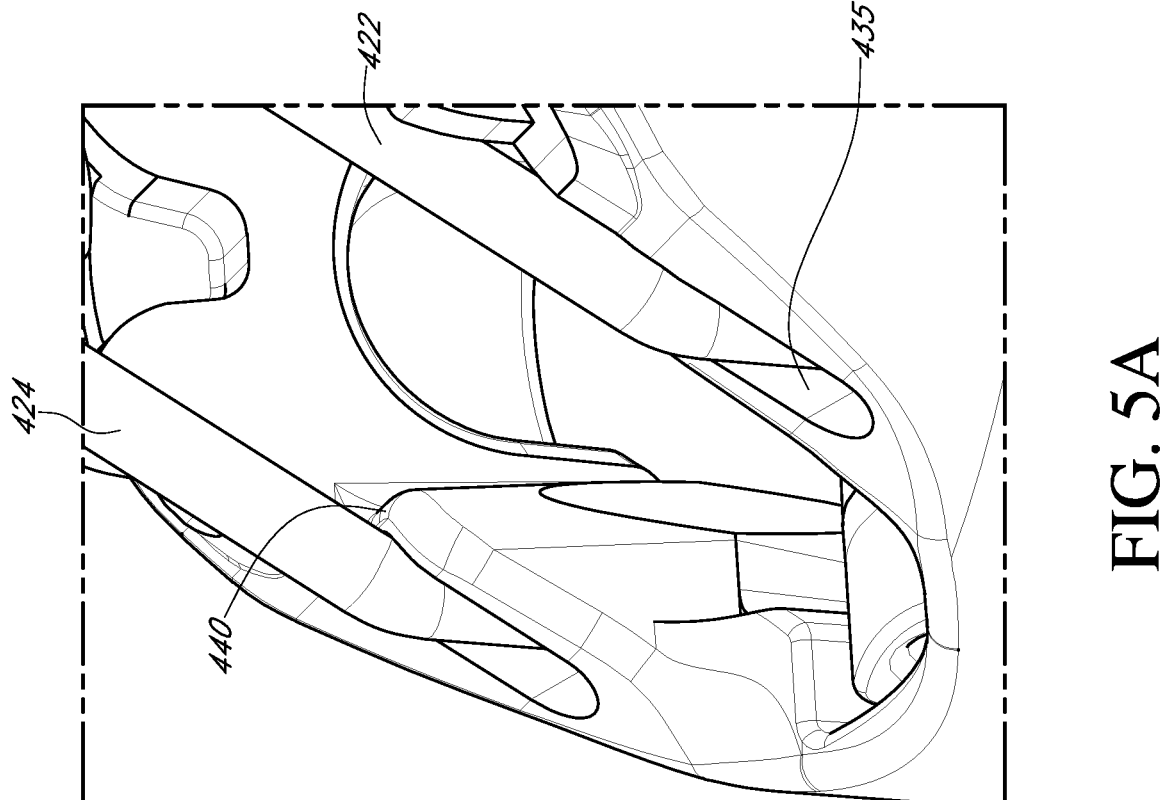
FIGS. 5A and 5B are detailed perspective views of the joint structure of FIG. 3 showing outer and inner actuation elements exiting a proximal link and extending across the joint in an articulated position of the joint structure.
Figure 5B:
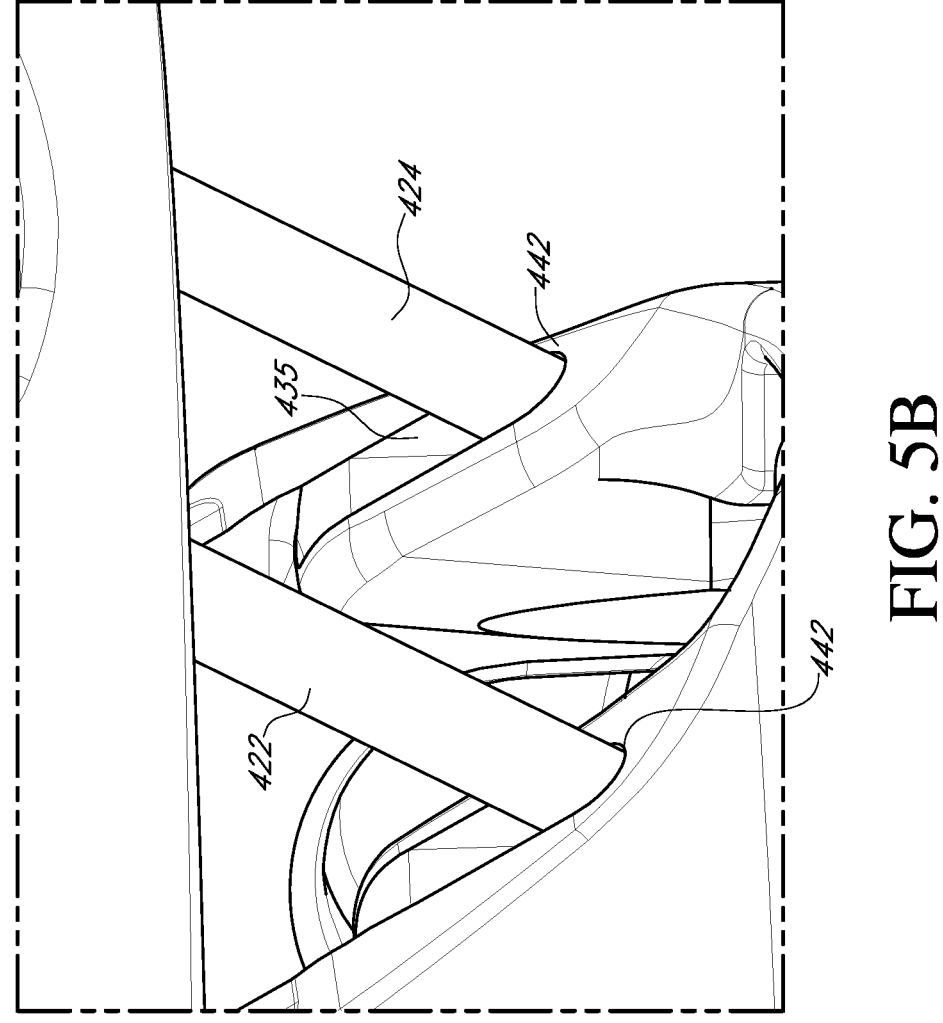

FIGS. 5A and 5B show detailed perspective views of the joint structure of FIG. 3 in an articulated position. In FIG. 5A, the outer (i.e., convex) side of the articulated joint structure is shown, and the actuation elements 422 and 424 rest on the actuation element guide channel inner portions 440 as discussed above in connection with FIG. 3. In FIG. 5B, the inner (i.e., concave) side of the articulated joint structure is shown, and the actuation elements 422 and 424 rest on the actuation element guide channel outer portions 442. In FIGS. 5A and 5B, the generally ovoid shape of the actuation element guide channels 435 is apparent. While the actuation element guide channels 435 in FIGS. 3, 4, 5A, and 5B feature a generally round cross-sectional shape, guide channels according to exemplary embodiments of the disclosure can feature various non-round cross-sectional shapes as discussed above.

Figure 6:
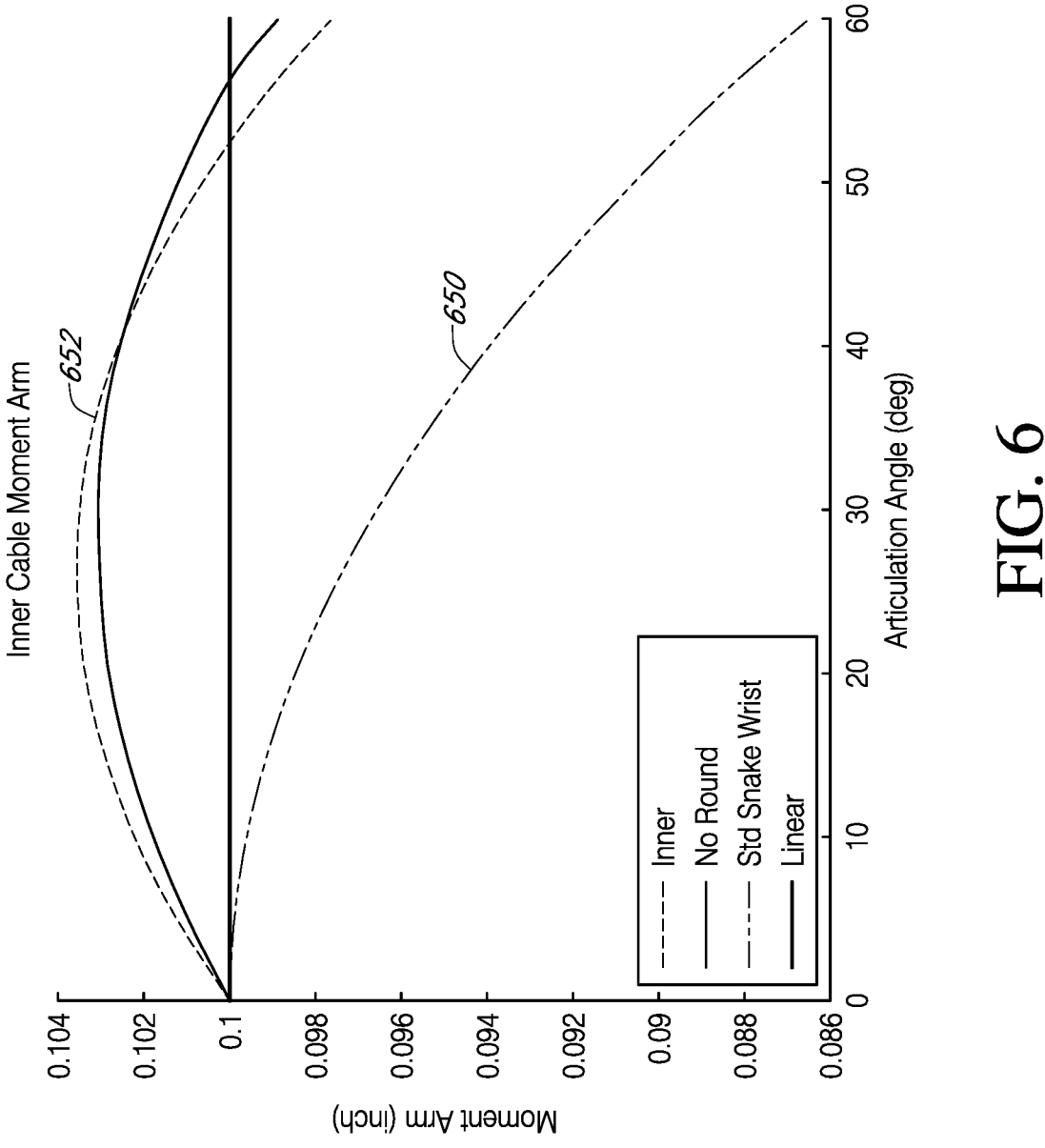
FIG. 6 is a chart showing actuation element moment arm versus articulation angle for a joint structure according to the present disclosure.

FIGS. 6-11 are charts displaying operational characteristics of various example configurations of joint structures according to the present disclosure tested by the inventors. Referring now to FIG. 6, a chart showing the moment arm of the inner actuation element (i.e., an actuation element located on the interior of the bend operational characteristics of a joint structure according to an exemplary embodiment of the present disclosure is shown. In this exemplary embodiment, the radius is 0.033 inches (0.838 mm). As discussed above, $D_1$ and $D_2$ are chosen to be unequal in this embodiment, e.g., to absorb any slack generated as the joint structure is articulated. In this exemplary embodiment, $D_1$ is chosen to be 0.025 inches (0.635 mm) and $D_2$ is chosen to be 0.031 inches (0.787 mm). As shown in FIG. 6, the moment arm of the actuation element initially grows slightly from 0.1 inch (0.254 mm) as the joint structure is articulated, and only drops below 0.1 inches once articulation exceeds 50 degrees. Throughout the range of articulation from 0 to 60 degrees, the embodiment of FIG. 6 has a greater moment arm, as indicated by line 652, than the conventional design indicated by the dashed line 650.

Figure 7:
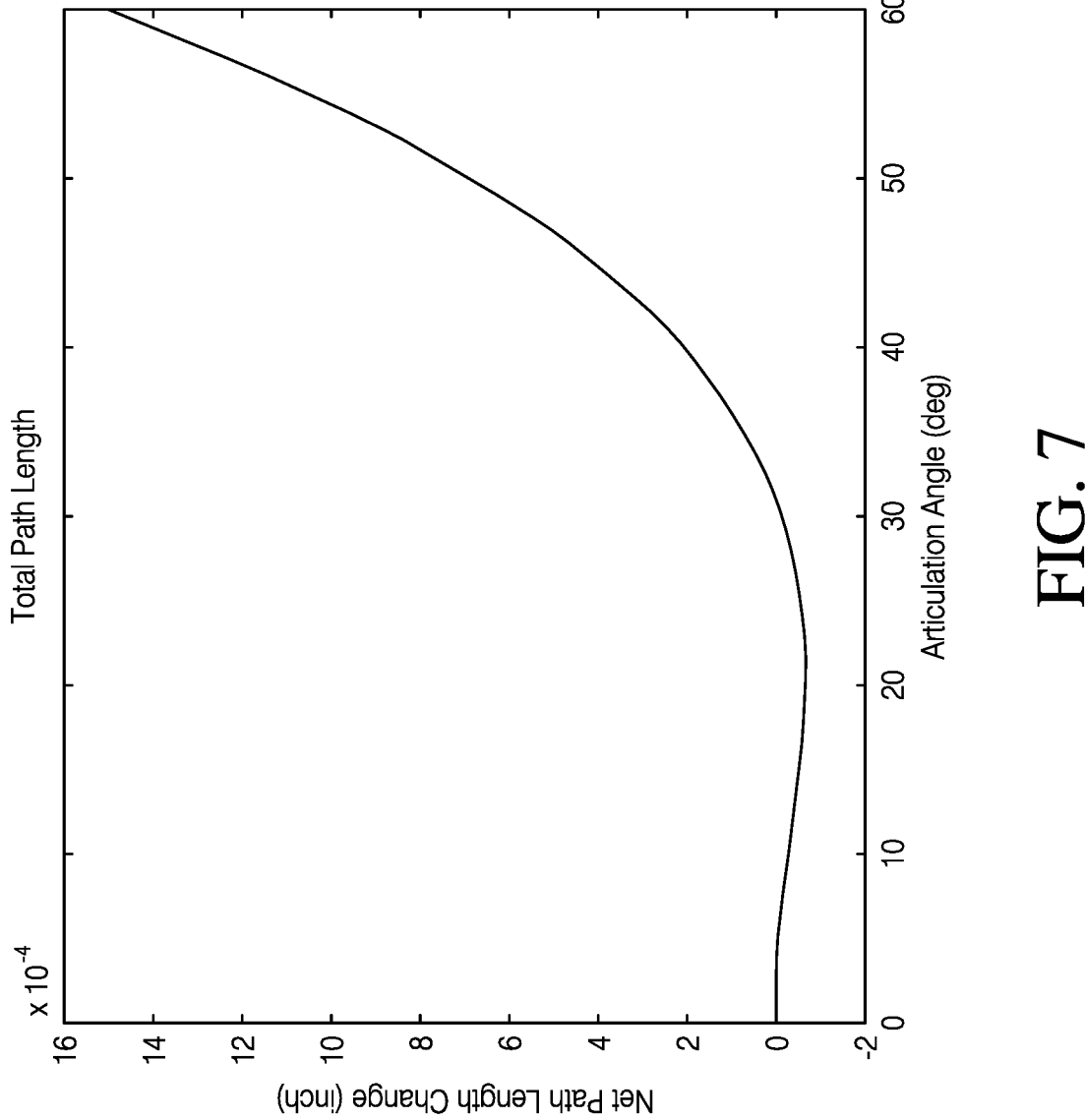
FIG. 7 is a chart showing actuation element path length versus articulation angle for an exemplary embodiment of a joint structure according to the present disclosure.

Referring now to FIG. 7, a chart illustrating the total path length of the actuation element passages as a function of articulation angle for the same embodiment as represented by FIG. 6 is shown. As shown in FIG. 7, as the articulation angle is increased beyond about 30 degrees, the total path length begins to increase. As discussed above, such path length increases can compensate for slack development due to high forces on the inner actuation element as the joint structure is articulated.

Figure 8:
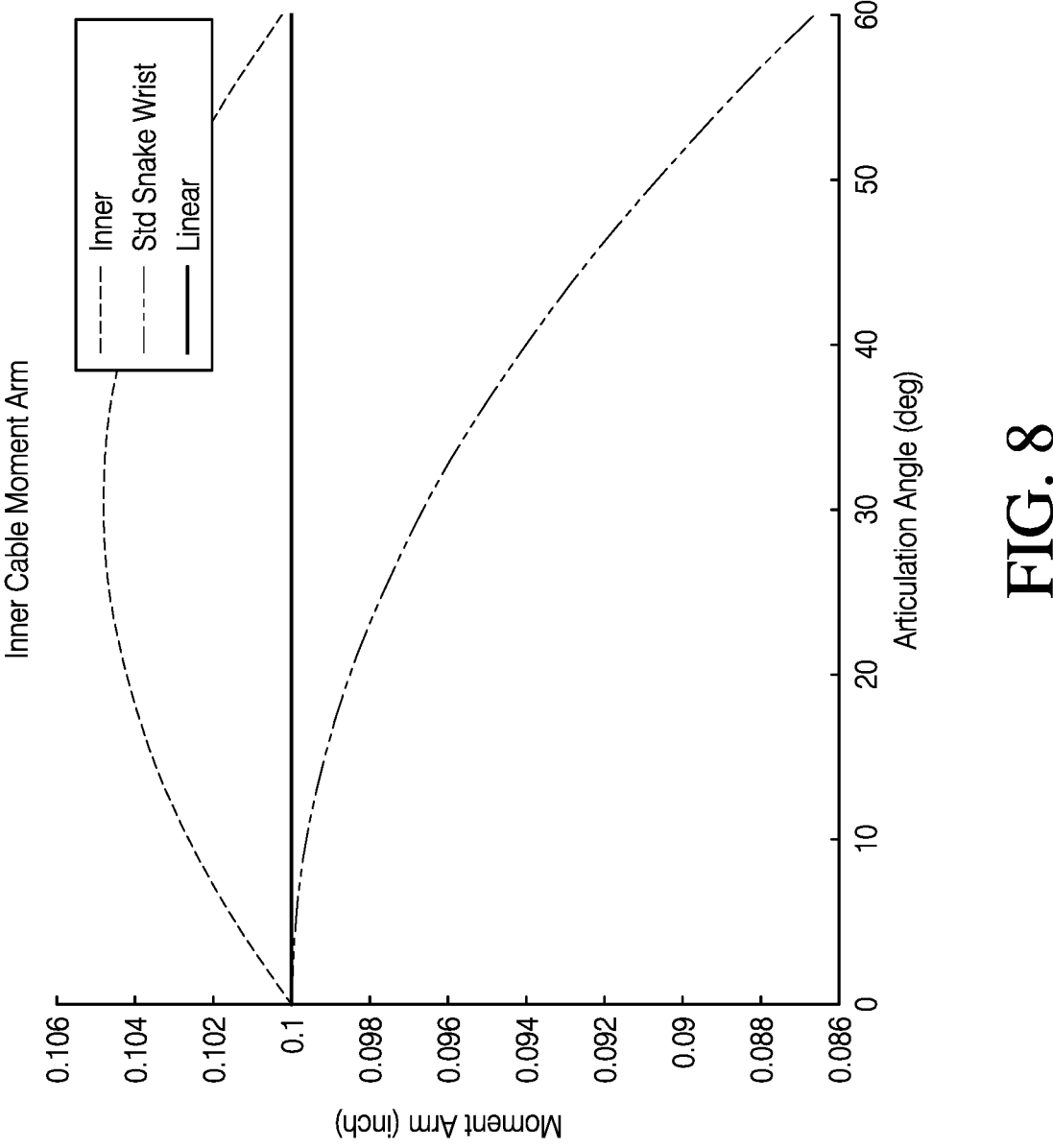
FIG. 8 is a chart showing actuation element moment arm versus articulation angle for another exemplary embodiment of a joint structure according to the present disclosure.

FIG. 8 is a chart showing moment arm length as a function of articulation angle of the joint structure for another exemplary embodiment of a joint structure according to the present disclosure. In this embodiment, $D_1$ and $D_2$ are nearly equal, with $D_1$ being 0.036 inches (0.914 mm) and $D_2$ 0.0361 inches (0.917 mm). This arrangement provides increased joint structure stiffness as discussed above as a result of the increased moment arm throughout the range of articulation of the joint structure. Like the embodiment associated with FIGS. 6 and 7, the embodiment of FIG. 8 includes radiused actuation element exits with a radius of 0.033 inches (0.838 mm). As shown in FIG. 8, the inner actuation element moment arm remains equal to or above 0.1 inches (0.254 mm) throughout the range of articulation of the joint structure from 0 to 60 degrees.

Figure 9:
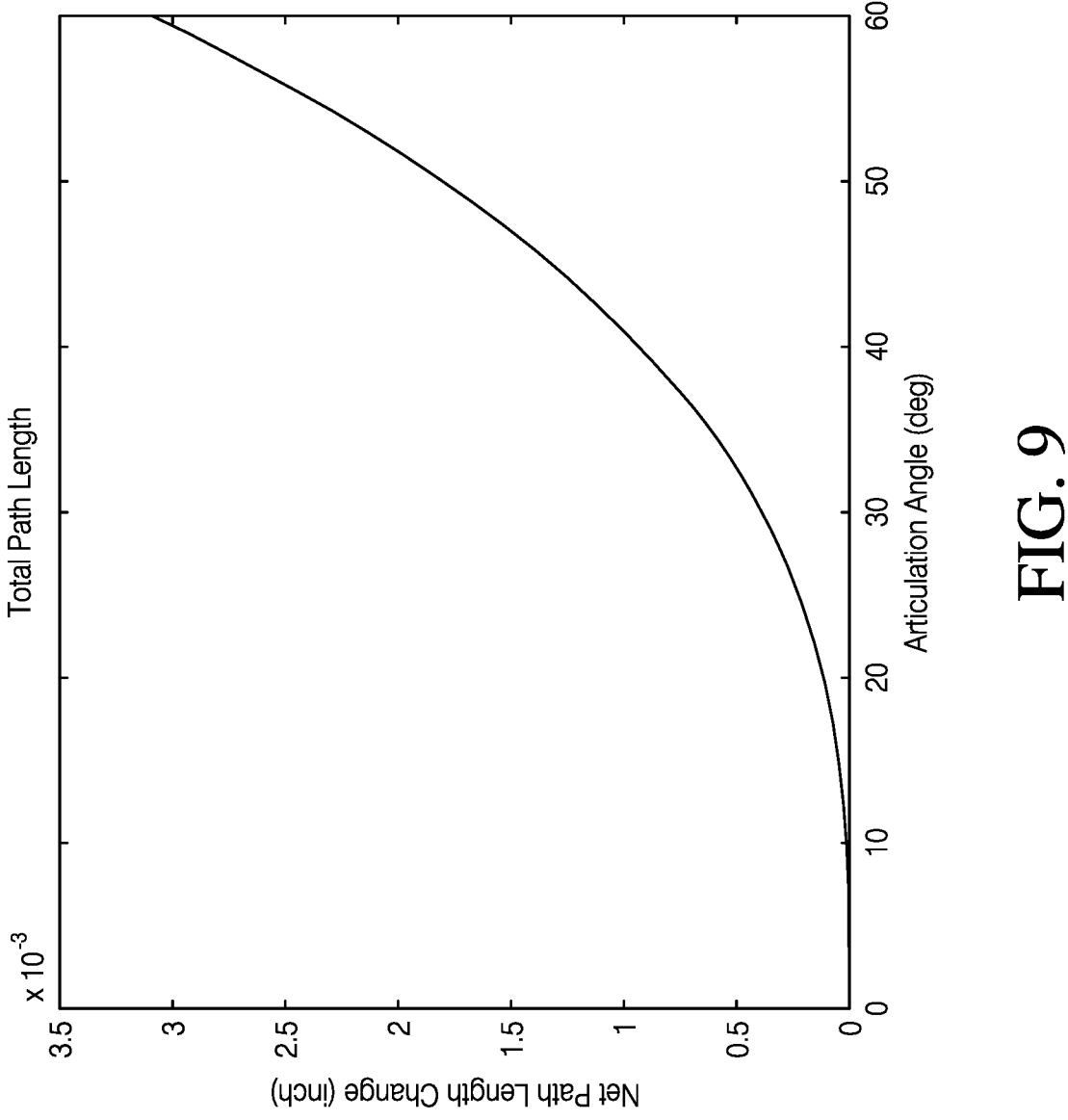
FIG. 9 is a chart showing actuation element path length versus articulation angle for another exemplary embodiment of a joint structure according to the present disclosure.

Referring now to FIG. 9, the total path length change over the range of articulation from 0 degrees to 60 degrees is only 0.003 inches (0.0762 mm) and this arrangement nearly provides perfect length conservation over the 60 degrees of articulation. Such an arrangement may be advantageous in situations in which a greater moment arm is desired over potential slack consumption.

Figure 10:
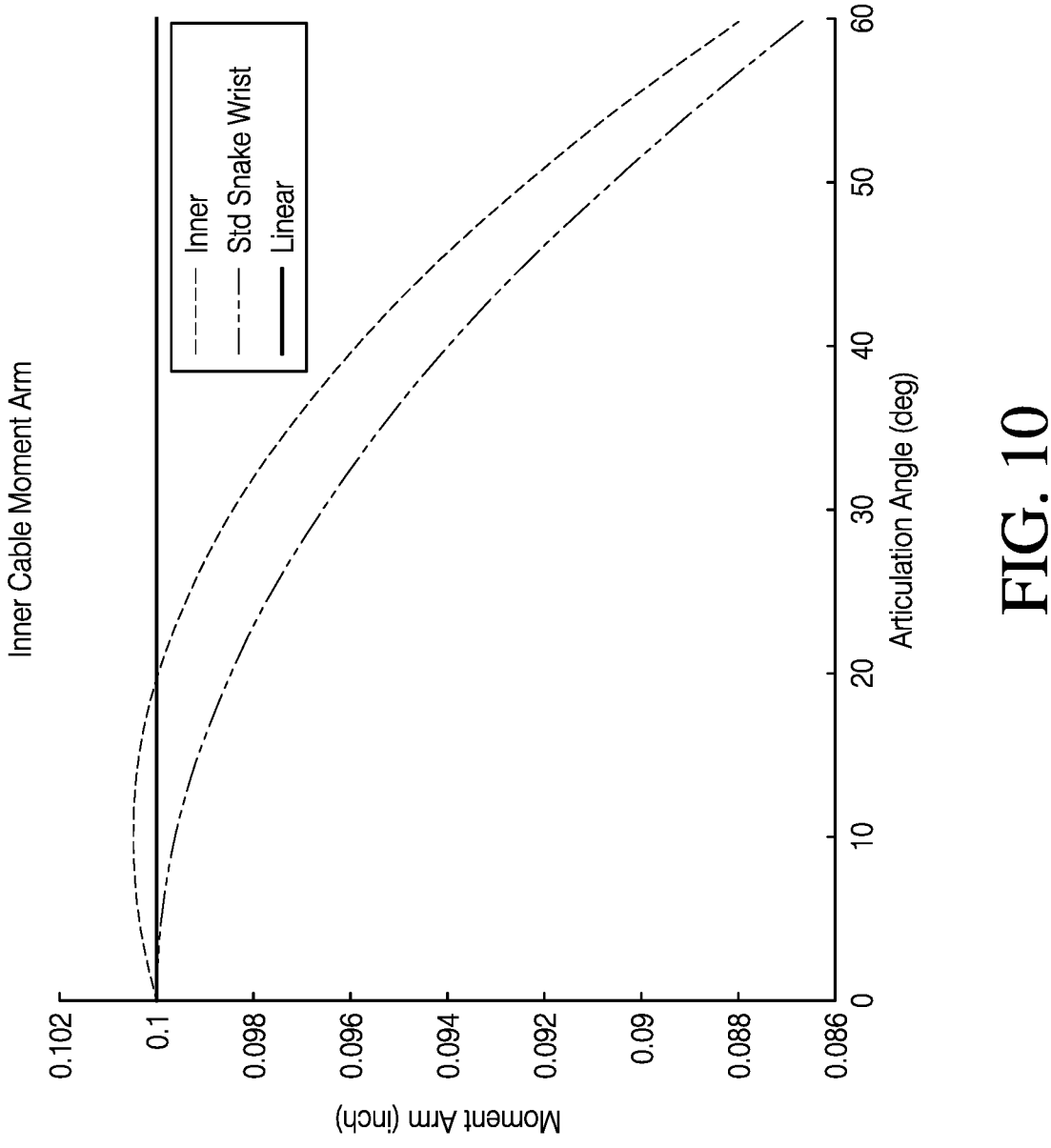
FIG. 10 is a chart showing actuation element moment arm versus articulation angle for another exemplary embodiment of a joint structure according to the present disclosure.
Figure 11:
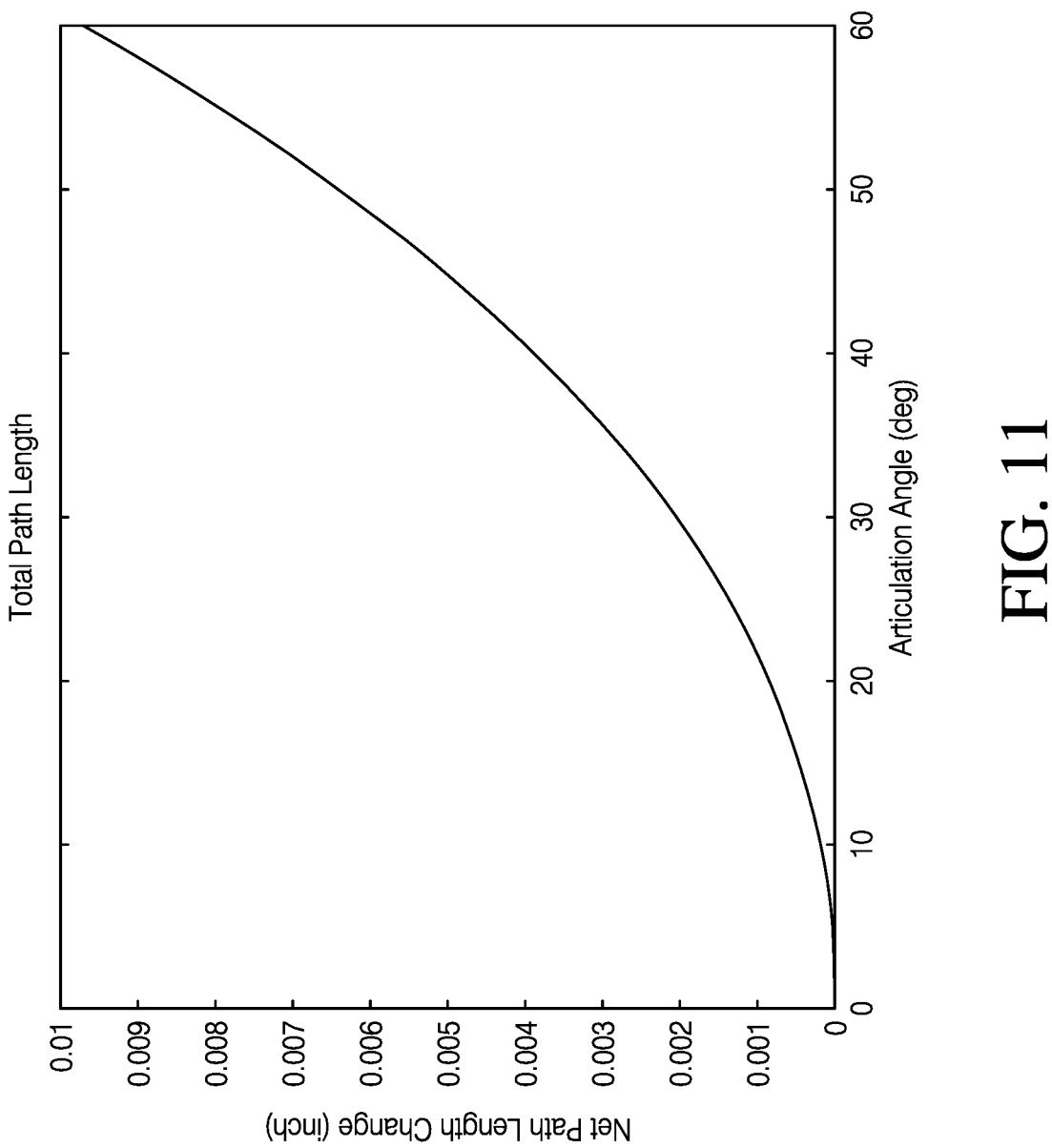
FIG. 11 is a chart showing actuation element path length versus articulation angle for another exemplary embodiment of a joint structure according to the present disclosure.

FIGS. 10 and 11 are charts illustrating characteristics associated with another exemplary embodiment of a joint structure according to the present disclosure. In this embodiment, the offset distances of the actuation element guide exits are chosen to provide an increase in path length as the joint structure is articulated. For example, the embodiment represented by the charts of FIGS. 10 and 11 features a $D_1$ dimension of 0.036 inches (0.9144 mm) and a dimension $D_2$ of 0.0115 inches (0.292 mm). Like the embodiments associated with FIGS. 6-9, this embodiment also features a radius of 0.033 inches (0.838 mm) at the actuation element exits.

As shown in FIG. 10, the inner actuation element moment arm is greater over the range of articulation that the moment arm of a conventional joint structure (labeled "Std Snake Wrist" in FIG. 10). However, the inner actuation element moment arm does begin to drop from the initial value of 0.1 inch (0.254 mm) at the initial, 0 degree of articulation position as the amount of articulation exceeds about 20 degrees. Referring to FIG. 11, the total path length increases throughout the range of articulation from 0 to 60 degrees, and at 60 degrees of articulation approaches 0.01 inches (0.254 mm). As discussed above, this arrangement can compensate for slack development in the outer actuation element as the joint structure is articulated, while still providing an increase in moment arm over the conventional design.

In addition to the slack consumption and joint structure stiffness effects provided by using the asymmetrical actuation element paths across a joint, altering the actuation element paths across a joint according to various embodiments described above can also reduce the likelihood of mechanical interference between the joint structure components and features of the environment in which devices including the joint structure are used. For example, referring again to FIG. 2, in an articulated position, the intermeshing components 218 and 220 extend beyond the actuation element 224. Under some conditions, contact between the intermeshing components 218 and 220 and, e.g., tissue surrounding an operation site in which an instrument including the joint structure is used could potentially result in undesirable interference between the intermeshing components and the surrounding tissue.

As shown in FIG. 3, in an articulated position, the actuation element 424 of the joint structure according to exemplary embodiments of the disclosure is positioned outboard of the intermeshing components 418 and 420, due to the inner actuation element guide portions 440 extending beyond the axes $A_{R1}$ and $A_{R2}$. In this way, the likelihood of tissue or other environmental materials interfering with the intermeshing components 418 and 420 is lessened.

Exemplary embodiments of joint structures according to the disclosure can include additional features configured to avoid interference between the joint structure components and surrounding environmental materials. For example, in some embodiments, instruments including joint structures according to embodiments of the disclosure can include flexible sheaths, sleeves, or other exterior protective components to prevent environmental materials from interfering between components of the joint structure. However, such sleeves can contribute to an increased overall diameter of the instrument. Thus, in some exemplary embodiments, particularly embodiments of instruments configured for minimally invasive surgical procedures, the components can include features configured to mitigate such interference without any sleeves or other exterior protective components. For example, referring now to FIG. 12, a perspective view of a joint structure 1252 is shown. The joint structure 1252 includes a joint 1254 between a first link 1255 and a second link 1256. The joint 1254 includes rolling contact surfaces 1216 that define the motion of the joint 1254. Under some conditions, environmental materials, such as tissue, can interfere with the rolling contact surfaces 1216, such as becoming pinched between opposing contact surfaces 1216.

Figure 13:
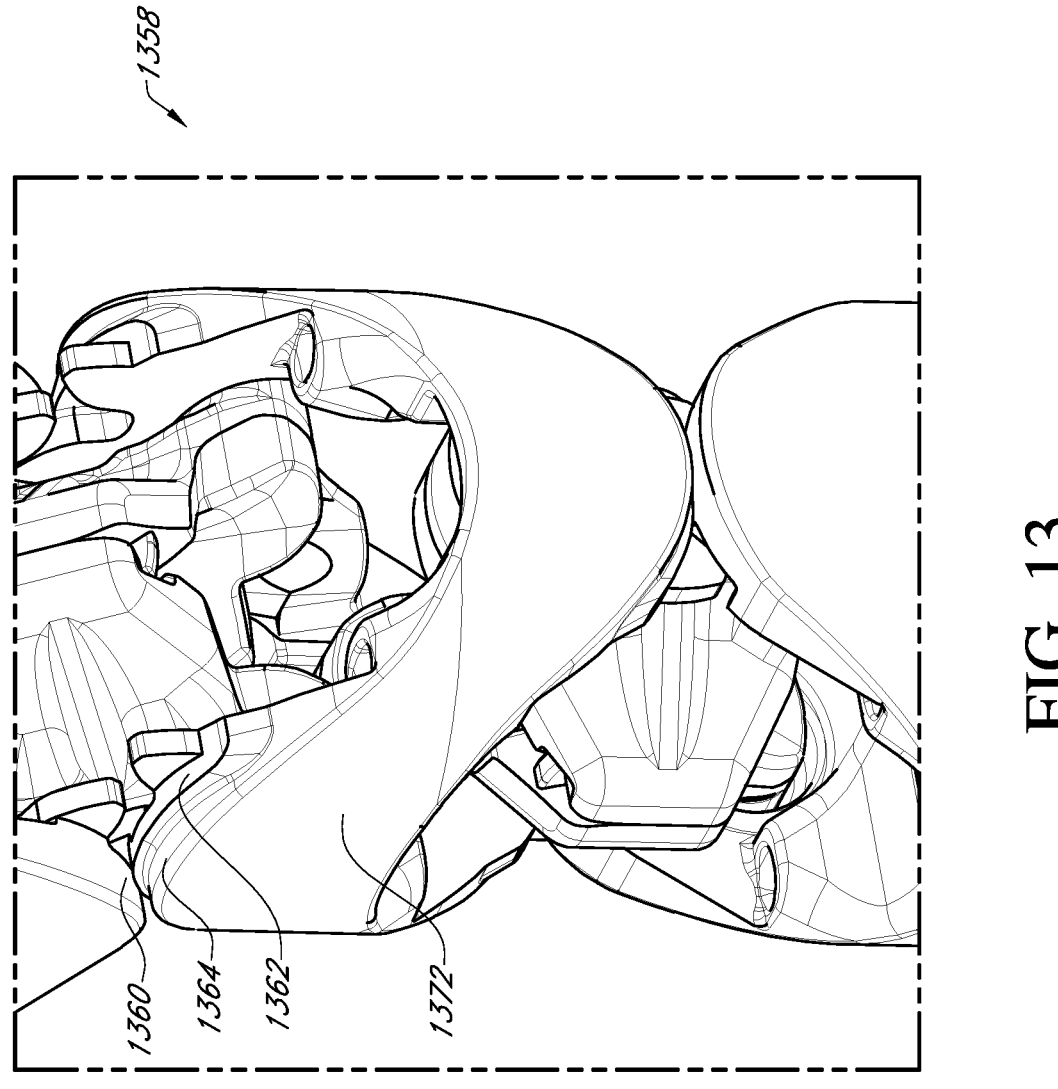
FIG. 13 is a perspective view of another embodiment of a joint structure according to the present disclosure.
Figure 14:
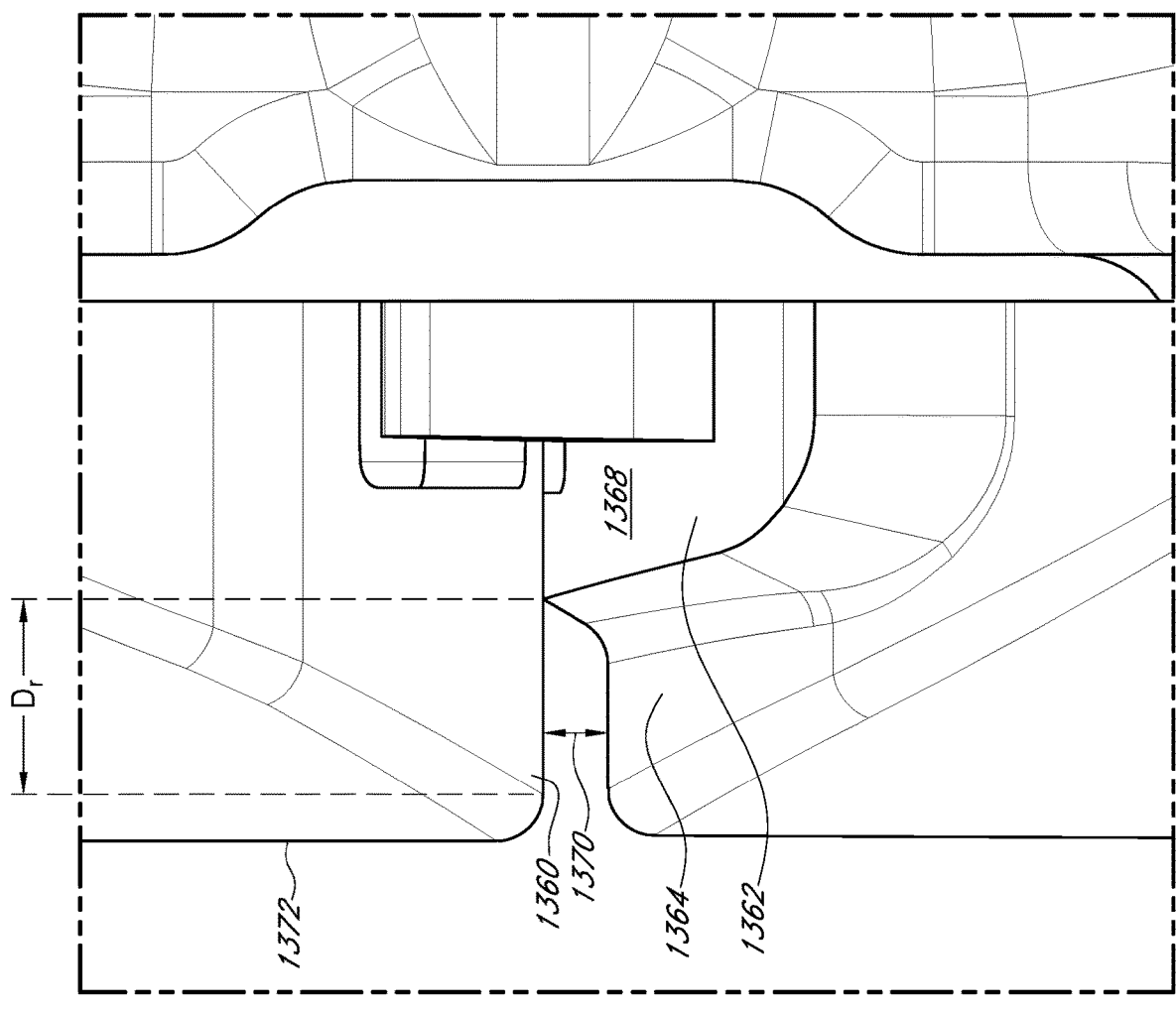
FIG. 14 is a side view of the joint structure of FIG. 13.

Embodiments of the disclosure can include features configured to reduce the likelihood of interference of environmental materials between the rolling contact surfaces 1216. For example, referring now to FIGS. 13 and 14, a joint structure 1358 includes rolling contact surfaces 1360 and 1362, of which one or both may be radially inward relative to an adjacent relieved portion. In the exemplary embodiment of FIG. 13, the rolling contact surface 1362 is adjacent a relieved portion 1364, while the rolling contact surface 1360 does not have any adjacent relieved portion. As shown in FIG. 14, the relieved portion 1364 creates a gap 1370 between rolling contact surface 1360 and the relieved portion 1364. A contact area 1368 of the rolling contact surface 1362 contacts the rolling contact surface 1360 to define movement of and support relative rotation between the joint structure components. Stated differently, the relieved portion 1364 creates a surface portion of the rolling contact surface 1362 that is spaced from the opposing rolling contact surface 1360 adjacent to an outer surface 1372 of the joint structure 1358.

The gap 1370 between the rolling contact surfaces 1360 and 1362 prevents environmental materials (such as tissue) from being caught or pinched between the rolling contact surface 1360 and contact area 1368 of the rolling contact surface 1362. The gap 1370 can be in a range from about 0.001 inches (0.0254 mm) to about 0.01 inches (0.254 mm) or more. In one exemplary embodiment, the gap 1370 is about 0.007 inches (0.178 mm).

The gap 1370 extends a radial distance $D_r$ from an outside surface 1372 of the joint structure 1358 inward to the contact area 1368 of the rolling contact surface 1362. The radial distance $D_r$ may be chosen to be greater than the size of the gap 1370 to provide a sufficient "buffer zone" to prevent environmental materials (such as tissue) from interfering with (e.g., being pinched by) the contact area 1368 and the rolling contact surface 1362. In the embodiment of FIGS. 13 and 14, the radial distance $D_r$ is greater than twice the size of the gap 1370, i.e., the radial distance $D_r$ is about 0.014 inches (0.0356 mm) or more. In other exemplary embodiments, the radial distance $D_r$ can be less than the value of the gap 1370, less than twice the value of the gap 1370, greater than twice the value of the gap 1370, or other values.

Figure 12:
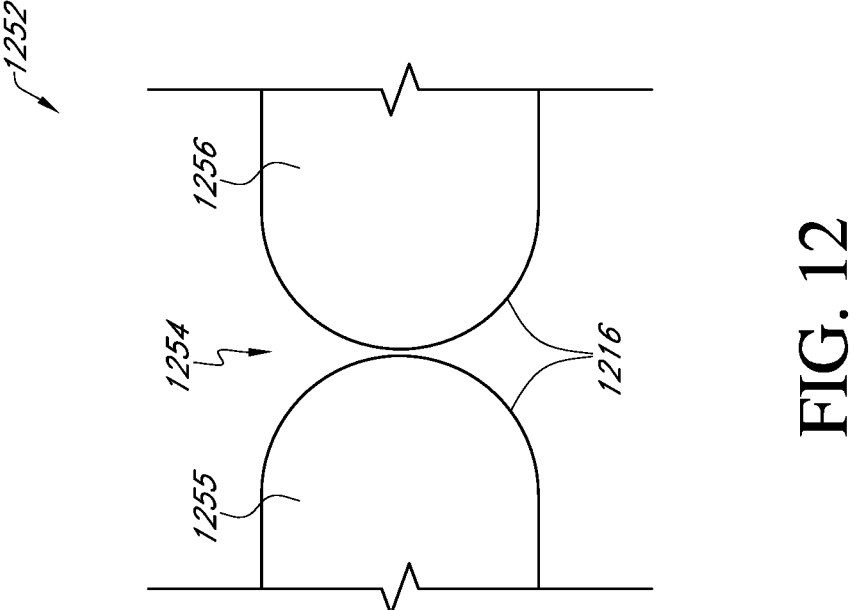
FIG. 12 is a schematic view of another embodiment of a joint structure according to the present disclosure.

Because the gap 1370 results in a contact area 1368 with less surface area than a comparable rolling contact surface without the gap 1370, the stress levels present on the contact area 1368 and corresponding areas of the rolling contact surface 1360 can potentially be greater than in the design of FIG. 12. To compensate for the greater stress levels, the joint structure components can be made from materials having a compressive strength sufficient to withstand the greater pressure levels present between components due to the gap 1370. Additionally, the contact area 1368 and the rolling contact surface 1360 can be processed to provide a greater strength, such as by heat treatment, surface modifications such as polishing, plating with various wear-resistant materials, or other manufacturing processes.

In the exemplary embodiment of FIG. 13, the rolling contact surface 1362 includes the relieved portion 1364, while the rolling contact surface 1360 is unrelieved. In other embodiments, the arrangement can be reversed, i.e., the rolling contact surface 1360 can include the relieved portion 1364 while the rolling contact surface 1362 can be unrelieved. In other exemplary embodiments, both the rolling contact surfaces 1360 and 1362 can include a similar relieved portion.

Exemplary embodiments of the present disclosure provide joint structures having improved stiffness and/or actuation element slack compensation as compared to conventional joints. Such joints can also include features that can lessen the likelihood of environmental materials (such as tissue, e.g., during a surgical procedure) from interfering with the mechanical operation of the joint structure.

Instruments including the embodiments described herein may be used, for example, with remotely operated, computer-assisted surgical systems employing robotic technology such as, for example, with a DA VINCI® Surgical System, such as the DA VINCI SI® Surgical System or the DA VINCI XI® Surgical System, Da Vinci SP, and Ion, both with or without Single-Site® single orifice surgery technology, all commercialized by Intuitive Surgical, Inc. of Sunnyvale, California Although various embodiments described herein are discussed with regard to surgical instruments used with a manipulating system of a computer-assisted surgical system employing robotic technology, the present disclosure is not limited to use with surgical instruments for such surgical systems. For example, various embodiments described herein can optionally be used in conjunction with hand-held, manual or semi-automated surgical instruments, such as those used for manual laparoscopic surgery, or other surgical and non-surgical instruments.

As discussed above, in accordance with various embodiments, surgical instruments of the present disclosure are configured for use in teleoperated, computer-assisted surgical systems employing robotic technology (sometimes referred to as robotic surgical systems). Referring now to FIG. 15, an embodiment of a manipulating system 1500 of a computer-assisted surgical system, to which surgical instruments are configured to be mounted for use, is shown. Such a surgical system may further include a user control system, such as a surgeon console (not shown) for receiving input from a user to control instruments coupled to the manipulating system 1500, as well as an auxiliary system, such as auxiliary systems associated with the DA VINCI SI® and DA VINCI XI®, Da Vinci SP, and Ion systems noted above.

As shown in the embodiment of FIG. 15, the manipulating system 1500 includes a base 1520, a main column 1540, and a main boom 1560 connected to main column 1540. Manipulating system 1500 also includes a plurality of manipulator arms 1510, 1511, 1512, 1513, which are each connected to main boom 1560. Manipulator arms 1510, 1511, 1512, 1513 each include an instrument mount portion 1522 to which an instrument 1530 may be mounted, which is illustrated as being attached to arm 1510.

Instrument mount portion 1522 comprises a drive assembly 1523 and a cannula mount 1524, with a transmission mechanism 1534 (which may generally correspond to the transmission mechanism 102 discussed in connection with FIG. 1A) of the instrument 1530 connecting with the drive assembly 1523, according to an embodiment. Cannula mount 1524 is configured to hold a cannula 1536 through which a shaft 1532 of instrument 1530 may extend to a surgery site during a surgical procedure. Although the embodiment of FIG. 15 shows an instrument 1530 attached to only manipulator arm 1510 for ease of viewing, an instrument may be attached to any and each of manipulator arms 1510, 1511, 1512, 1513.

Other configurations of surgical systems, such as surgical systems configured for single-port surgery, are also contemplated. For example, with reference now to FIG. 16, a portion of an embodiment of a manipulator arm 2140 of a manipulating system with two surgical instruments 2300, 2310 in an installed position is shown. The surgical instruments 2300, 2310 can generally correspond to instruments discussed above, such as instrument 100 disclosed in connection with FIG. 1. For example, the embodiments described herein may be used with a DA VINCI SP® Surgical System, commercialized by Intuitive Surgical, Inc. of Sunnyvale, California. The schematic illustration of FIG. 16 depicts only two surgical instruments for simplicity, but more than two surgical instruments may be mounted in an installed position at a manipulating system as those having ordinary skill in the art are familiar with. Each surgical instrument 2300, 2310 includes a shaft 2320, 2330 that at a distal end has a moveable end effector or an endoscope, camera, or other sensing device, and may or may not include a wrist mechanism (not shown) to control the movement of the distal end.

In the embodiment of FIG. 16, the distal end portions of the surgical instruments 2300, 2310 are received through a single port structure 2380 to be introduced into the patient. As shown, the port structure includes a cannula and an instrument entry guide inserted into the cannula. Individual instruments are inserted into the entry guide to reach a surgical site.

Other configurations of manipulating systems that can be used in conjunction with the present disclosure can use several individual manipulator arms. In addition, individual manipulator arms may include a single instrument or a plurality of instruments. Further, as discussed above, an instrument may be a surgical instrument with an end effector or may be a camera instrument or other sensing instrument utilized during a surgical procedure to provide information, (e.g., visualization, electrophysiological activity, pressure, fluid flow, and/or other sensed data) of a remote surgical site.

Transmission mechanisms 2385, 2390 (which may generally correspond to transmission mechanism 102 disclosed in connection with FIG. 1A) are disposed at a proximal end of each shaft 2320, 2330 and connect through a sterile adaptor 2400, 2410 with drive assemblies 2420, 2430. Drive assemblies 2420, 2430 contain a variety of internal mechanisms (not shown) that are controlled by a controller (e.g., at a control cart of a surgical system) to respond to input commands at a surgeon side console of a surgical system to transmit forces to the transmission mechanisms 2385, 2390 to actuate surgical instruments 2300, 2310.

The embodiments described herein are not limited to the embodiments of FIG. 15 and FIG. 16, and various other teleoperated, computer-assisted surgical system configurations may be used with the embodiments described herein. The diameter or diameters of an instrument shaft, wrist mechanism, and end effector are generally selected according to the size of the cannula with which the instrument will be used and depending on the surgical procedures being performed.

This description and the accompanying drawings that illustrate exemplary embodiments should not be taken as limiting. Various mechanical, compositional, structural, electrical, and operational changes may be made without departing from the scope of this description and the invention as claimed, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are non-limiting, and modifications to structure, dimensions, materials, and methodologies may be made without departing from the scope of the present teachings.

Other embodiments in accordance with the present disclosure will be apparent to those skilled in the art from consideration of the specification and practice of the invention disclosed herein. It is intended that the specification and examples be considered as exemplary only, with the following claims being entitled to their fullest breadth, including equivalents, under the applicable law.

What is claimed is:

1. A joint structure of an instrument, comprising:
a first link and a second link coupled to one another by a joint, the first link and the second link being articulatable relative to each other about the joint, and the first link being proximal the second link; and
an actuation element extending through a first guide channel in the first link and a second guide channel in the second link, wherein the actuation element causes articulating of the first link and the second link relative to each other about the joint in response to tension applied on the actuation element in a proximal direction with respect to the instrument;
wherein:
the first guide channel terminates in an opening where the actuation element extends from the first link to extend across the joint to the second link, a first edge portion of the opening being at a first location along a longitudinal axis of the first guide channel and a second edge portion of the opening being at a second location along the longitudinal axis of the first guide channel, the first location being on a first side of a plane intersecting a rotational axis of the first link about the joint and the second location being on a second side of the plane opposite the first side.

2. The joint structure of claim 1, wherein:
the plane is a first plane; and
the second guide channel terminates in a second opening where the actuation element extends from the second link to extend across the joint to the first link, a first edge portion of the second opening being at a first location along a longitudinal axis of the second guide channel, and a second edge portion of the opening being at a second location along the longitudinal axis of the second guide channel, the first location being on a first side of a second plane intersecting a rotational axis of the second link about the joint and the second location being on a second side of the second plane.

3. The joint structure of claim 1, wherein the first location along the longitudinal axis is offset from the plane a first distance, and the second location along the longitudinal axis is offset from the plane a second distance.

4. The joint structure of claim 3, wherein the first distance is equal to the second distance.

5. The joint structure of claim 3, wherein the first distance is different from the second distance.

6. The joint structure of claim 1, wherein at least one of the first edge portion and the second edge portion of the first guide channel comprise a radiused portion.

7. The joint structure of claim 1, wherein the first link and the second link contact one another along complementary rolling contact surfaces comprising an at least partially cylindrical surface profile.

8. The joint structure of claim 7, wherein the first link and the second link comprise intermeshing features that prevent slippage of the complementary rolling contact surfaces relative to one another.

9. The joint structure of claim 8, wherein in an articulated state of the joint, the actuation element is positioned radially outward from the intermeshing features.

10. The joint structure of claim 9, wherein one of the first link and the second link comprises a relieved surface adjacent to and radially outward from the rolling contact surface, the relieved surface facing a rolling contact surface of the other of the first link and the second link.

11. The joint structure of claim 10, wherein the relieved surface defines a gap between the rolling contact surface and the relieved surface.

12. A medical device comprising:
a first link and a second link disposed in series in a proximal-to-distal direction with respect to the medical device and defining an articulatable member; and
an actuation element extending in the proximal-to-distal direction through a first guide channel of the first link and through a second guide channel of the second link;
wherein, in an unarticulated state of the articulatable member, a portion of the actuation element between the first guide channel of the first link and the second guide channel of the second link is positioned a first radial distance from a longitudinal centerline of the articulatable member,
wherein, in an articulated state of the articulatable member and on a convex side of an articulated shape of the articulatable member, the portion of the actuation element between the first guide channel of the first link and the second guide channel of the second link is positioned a second radial distance from the longitudinal centerline of the articulatable member, and
wherein the second radial distance is greater than the first radial distance.

13. The medical device of claim 12, wherein the articulated state comprises a range of bend angles greater than zero degrees and equal to or less than 60 degrees.

14. The medical device of claim 12, wherein the articulated state comprises a range of bend angles greater than zero degrees and equal to or less than 30 degrees.

15. The medical device of claim 12, wherein, in the articulated state of the articulatable member and on a concave side of the articulated shape of the articulatable member, a portion of the actuation element between a third guide channel of the first link and a fourth guide channel of the second link is positioned the second radial distance from the longitudinal centerline of the articulatable member.

16. A joint structure of an instrument, comprising:
a first link and a second link coupled to one another by a joint, the first link and the second link being articulatable relative to each other about the joint, and the first link being proximal the second link; and
an actuation element extending through a first guide channel in the first link and a second guide channel in the second link, wherein the actuation element causes articulating of the first link and the second link relative to each other about the joint in response to tension applied on the actuation element in a proximal direction with respect to the instrument;
wherein:
on a condition the joint structure is in an articulated state, the actuation element lies at a first radial distance from a centerline of the joint on a condition the actuation element is on a concave side of the joint structure, and the actuation element lies at a second radial distance from the centerline of the joint on a condition the actuation element is on a convex side of the joint structure, the second radial distance being different from the first radial distance.

17. The joint structure of claim 16, wherein an opening of the first guide channel defines a first edge portion of the opening at a first location along a longitudinal axis of the first guide channel and a second edge portion of the opening at a second location different from the first location along the longitudinal axis of the first guide channel.

18. The joint structure of claim 17, wherein the first edge portion is positioned radially outward relative to the second edge portion.

19. The joint structure of claim 17, wherein the first edge portion is positioned proximal of the second edge portion.

20. The joint structure of claim 17, wherein the first location along the longitudinal axis is on a first side of a plane intersecting a rotational axis of the first link about the joint and the second location along the longitudinal axis is on a second side opposite the first side of the plane.

\* \* \* \* \*